(12) United States Patent
Moore et al.

(10) Patent No.: US 9,211,274 B2
(45) Date of Patent: Dec. 15, 2015

(54) TRPV1 COMPOUNDS IN A BIODEGRADABLE POLYMER CARRIER

(75) Inventors: Nicholas A. Moore, Memphis, TN (US); Danielle L. Clay, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 229 days.

(21) Appl. No.: 13/363,469

(22) Filed: Feb. 1, 2012

(65) Prior Publication Data

US 2013/0197094 A1     Aug. 1, 2013

(51) Int. Cl.

| | |
|---|---|
| A61F 2/00 | (2006.01) |
| A61K 31/165 | (2006.01) |
| A61K 9/00 | (2006.01) |
| A61K 31/357 | (2006.01) |
| A61K 9/70 | (2006.01) |

(52) U.S. Cl.
CPC ............ *A61K 31/165* (2013.01); *A61K 9/0024* (2013.01); *A61K 9/70* (2013.01); *A61K 31/357* (2013.01)

(58) Field of Classification Search
None
See application file for complete search history.

(56) References Cited

U.S. PATENT DOCUMENTS

| | | | |
|---|---|---|---|
| 4,450,150 A * | 5/1984 | Sidman | 424/424 |
| 6,812,254 B1 | 11/2004 | Barr et al. | |
| 2006/0204561 A1 | 9/2006 | Muhammad et al. | |
| 2006/0240097 A1 | 10/2006 | Jamieson et al. | |
| 2006/0247791 A1 | 11/2006 | McKay et al. | |
| 2008/0058362 A1 | 3/2008 | Singh et al. | |
| 2009/0131532 A1 | 5/2009 | Flowers | |
| 2010/0120912 A1 | 5/2010 | Singh et al. | |
| 2010/0234470 A1 | 9/2010 | Sangameswaran et al. | |
| 2010/0292755 A1 | 11/2010 | Jones et al. | |
| 2011/0027331 A1 * | 2/2011 | Hobot | 424/422 |
| 2011/0039875 A1 | 2/2011 | Singh | |
| 2011/0218180 A1 | 9/2011 | Singh et al. | |
| 2011/0236459 A1 * | 9/2011 | Stopek et al. | 424/426 |

FOREIGN PATENT DOCUMENTS

WO     WO 98/40070    *    9/1998

OTHER PUBLICATIONS

FreeDictionary, Several, (accessed Oct. 15, 2013), pp. 1-3.*
Medical News Today, Innocoll Announces Initiation of Phase IIA Clinical Study of Bupivacaine Collagen Sponge (Mar. 29, 2006), pp. 1-5.*
JP 2008-069088, Inada, Masaki, et al. (Mar. 27, 2008), machine translation, pp. 1-9.*

* cited by examiner

Primary Examiner — Scott Long
Assistant Examiner — Lyndsey Beckhardt
(74) Attorney, Agent, or Firm — Sorell Lenna & Schmidt LLP

(57) ABSTRACT

Effective treatments of pain for extended periods of time are provided. Through the administration of an effective amount of a TRPV1 compound (e.g., capsaicinoid compound) at or near a target site, one can relieve pain caused by diverse sources, including but not limited to, postoperative pain, spinal disc herniation (i.e. sciatica), spondilothesis, stenosis, discogenic back pain and joint pain, as well as pain that is incidental to surgery. When appropriate formulations are provided within biodegradable polymers, this relief can be continued for at least three days. In some embodiments, the relief can be for at least twenty-five days, at least fifty days, at least one hundred days, at least one hundred and thirty-five days or at least one hundred and eighty days.

11 Claims, 2 Drawing Sheets

TRPV1 COMPOUNDS IN A BIODEGRADABLE POLYMER CARRIER

BACKGROUND

Pain is typically experienced when the free nerve endings of pain receptors are subject to mechanical, thermal, chemical or other noxious stimuli. These pain receptors can transmit signals along afferent neurons to the central nervous system and then to the brain. When a person feels pain, any one or more of a number of problems can be associated with this sensation, including but not limited to reduced function, reduced mobility, complication of sleep patterns, and decreased quality of life.

The causes of pain include but are not limited to inflammation, injury, disease, muscle stress, the onset of a neuropathic event or syndrome, and damage that can result from surgery or an adverse physical, chemical or thermal event or from infection by a biologic agent. When a tissue is damaged, a host of endogenous pain inducing substances, for example, bradykinin and histamine can be released from the injured tissue. The pain inducing substances can bind to receptors on the sensory nerve terminals and thereby initiate afferent pain signals. After activation of the primary sensory afferent neurons, the projection neurons may be activated. These neurons carry the signal via the spinothalamic tract to higher parts of the central nervous system.

One known class of pharmaceuticals to treat pain is opioids. This class of compounds is well-recognized as being among the most effective type of drugs for controlling pain, such as post-operative pain. Unfortunately, because opioids are administered systemically, the associated side effects raise significant concerns, including disabling the patient, depressing the respiratory system, constipation, and psychoactive effects such as sedation and euphoria, thereby instituting a hurdle to recovery and regained mobility. Consequently, physicians typically limit the administration of opioids to within the first twenty-four hours post-surgery. Thus, it would be preferable to use non-narcotic drugs that deliver direct, localized pain control at a surgical site.

One pharmaceutical class of compounds that is known to the medical profession is the compounds that target the vanilloid receptor. More particularly, the transient receptor potential cation channel subfamily V member 1 (TRPV1) compounds, which act on the nociceptors (c-fibers). One known TRPV1 receptor agonist is capsaicin, which belongs to the family of compounds known as capsaicinoids. In general, capsaicin, is also known as N-(4-hydroxy-3-methoxybenzyl)-8-methylnon-trans-6-enamide. Capsaicin is externally applied to the skin to provide temporary relieve of pain in the treatment of muscles aches and osteoarthritis. Humans have long been exposed to dietary sources of capsaicin-containing spices and to topical preparations used for a variety of medical indications. This vast experience has not revealed significant or lasting adverse effects of capsaicin exposure.

It would therefore be advantageous to provide methods and compositions including TRPV1 compounds with effective concentrations to cause an analgesic effect. Implantable devices containing TRPV1 compounds are needed.

SUMMARY

Compositions and methods are provided comprising a TRPV1 compound, that are administered in order to treat pain, post operation pain and/or inflammation. The TRPV1 compound (e.g., capsaicinoid compound) can be a TRPV1 prodrug (capsaicinoid prodrug). The compositions and methods provided may for example be used to treat pain due to, post-operative procedures, a spinal disc herniation (i.e., sciatica), spondilothesis, stenosis, osteoarthritis, carpal/tarsal tunnel syndrome, tendonitis, temporomandibular joint disorder (TMJ), discogenic back pain, joint pain or inflammation.

According to one embodiment, there is an implantable device comprising: a TRPV1 compound (e.g., capsaicinoid compound), wherein the TRPV1 compound (e.g., capsaicinoid compound) comprises from about 0.1 wt. % to about 30 wt. % of the formulation and at least one biodegradable polymer. In some embodiments, the implantable device can be a sponge matrix containing the TRPV1 compound (e.g., capsaicinoid compound) and can be implanted at or near the target tissue site.

In some embodiments, the drug depot comprises a TRPV1 compound (e.g., capsaicinoid compound) that is in the drug depot in an amount of from about 0.1% to about 75% by weight and the drug depot can be used to improve wound healing.

The implantable device may for example, be part of a drug depot. The drug depot may: (i) consist of only the TRPV1 compound (e.g., capsaicinoid compound) and the biodegradable polymer(s); or (ii) consist essentially of the TRPV1 compound (e.g., capsaicinoid compound) and the biodegradable polymer(s); or (iii) comprise the TRPV1 compound (e.g., capsaicinoid compound) and the biodegradable polymer(s) and one or more other active ingredients, surfactants, excipients or other ingredients or combinations thereof. When there are other active ingredients, surfactants, excipients or other ingredients or combinations thereof in the formulation, in some embodiments these other compounds or combinations thereof comprise less than 50 wt. %, less than 40 wt. %, less than 30 wt. %, less than 20 wt. %, less than 19 wt. %, less than 18 wt. %, less than 17 wt. %, less than 16 wt. %, less than 15 wt. %, less than 14 wt. %, less than 13 wt. %, less than 12 wt. %, less than 11 wt. %, less than 10 wt. %, less than 9 wt. %, less than 8 wt. %, less than 7 wt. %, less than 6 wt. %, less than 5 wt. %, less than 4 wt. %, less than 3 wt. %, less than 2 wt. %, less than 1 wt. % or less than 0.5 wt. %.

According to another embodiment, there is an implantable device for reducing, preventing or treating pain in a patient in need of such treatment, the implantable device comprising a TRPV1 compound (e.g., capsaicinoid compound) in an amount from about 0.1 wt. % to about 99 wt. % of the implantable device, and at least one biodegradable polymer, wherein the implantable device is capable of releasing the TRPV1 compound (e.g., capsaicinoid compound) over a period of at least three days.

According to another embodiment, there is an implantable drug depot for reducing, preventing or treating pain in a patient in need of such treatment, the implantable drug depot comprising a TRPV1 compound (e.g., capsaicinoid compound) in an amount of from about 0.1 wt. % to about 30 wt. % of the drug depot and at least one polymer wherein the at least one polymer comprises one or more of poly(lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone, L-lactide-co-caprolactone, D,L-lactide-co-caprolactone, D-lactide-co-caprolactone, or a combination thereof.

According to yet another embodiment, there is a method for treating acute pain, wherein said method comprises implanting a drug depot in an organism to reduce, prevent or treat pain, wherein said drug depot comprises a TRPV1 compound (e.g., capsaicinoid compound) in an amount from about 0.1 wt. % to about 30 wt. % of the drug depot and at least one biodegradable polymer.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1:
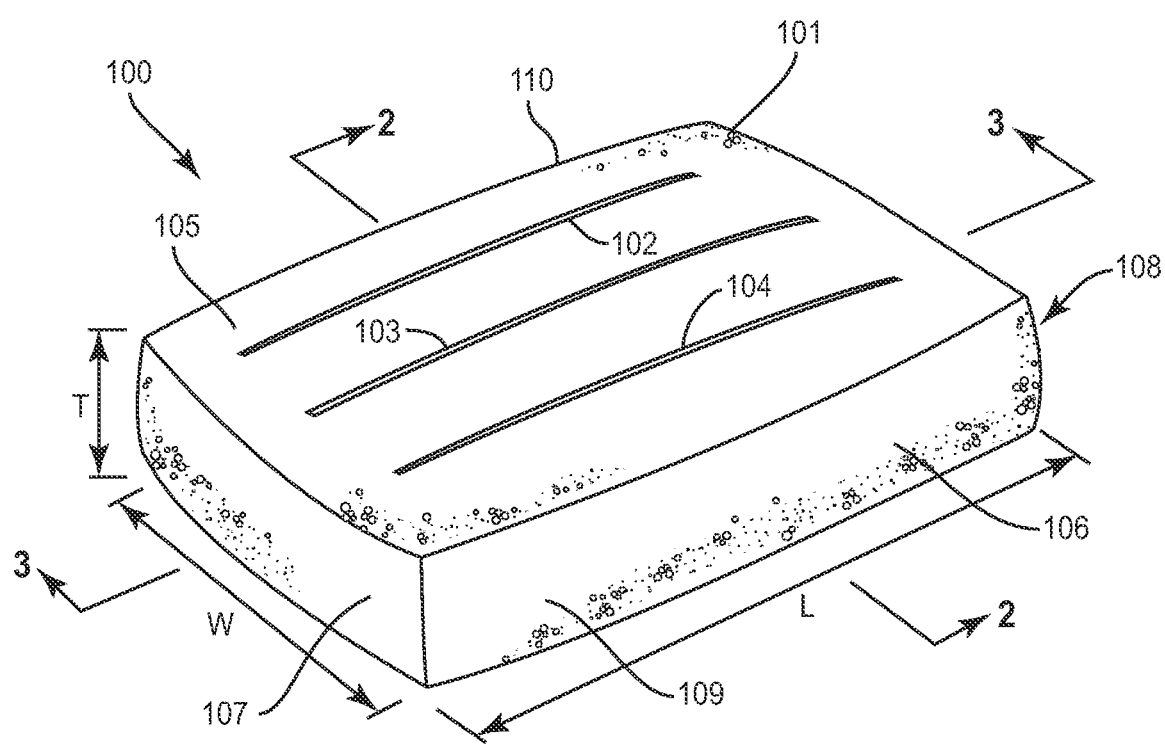
FIG. 1 depicts a perspective view of an exemplary drug depot shown as a matrix comprising an implant body defining a plurality of score lines according to an aspect of the present application.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

DEFINITIONS

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

A "drug depot" is the composition in which the capsaicinoid compound is administered to the body. Thus, a drug depot may comprise a physical structure to facilitate implantation and retention in a desired site (e.g., a disc space, a spinal canal, a tissue of the patient, particularly at or near a site of chronic pain, etc.). The drug depot may also comprise the drug itself. The term "drug" as used herein is generally meant to refer to any substance that alters the physiology of a patient. The term "drug" may be used interchangeably herein with the terms "therapeutic agent," "therapeutically effective amount," and "active pharmaceutical ingredient" or "API." It will be understood that unless otherwise specified a "drug" formulation may include more than one therapeutic agent, wherein exemplary combinations of therapeutic agents include a combination of two or more drugs. The drug provides a concentration gradient of the therapeutic agent for delivery to the site. In various embodiments, the drug depot provides an optimal drug concentration gradient of the therapeutic agent at a distance of up to about 0.01 cm to about 20 cm from the administration site and comprises a capsaicinoid compound. A drug depot includes, a matrix, a pump or pellet.

A "therapeutically effective amount" or "effective amount" is such that when administered, the drug results in alteration of the biological activity, such as, for example, inhibition of inflammation, reduction or alleviation of pain or spasticity, improvement in the condition through muscle relaxation, etc. The dosage administered to a patient can be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. In some embodiments the formulation is designed for immediate release. In other embodiments the formulation is designed for sustained release. In other embodiments, the formulation comprises one or more immediate release surfaces and one or more sustained release surfaces.

A "depot" includes but is not limited to capsules, microspheres, microparticles, microcapsules, microfibers particles, nanospheres, nanoparticles, coating, matrices, wafers, pills, pellets, emulsions, liposomes, micelles, gels, or other pharmaceutical delivery compositions or a combination thereof. Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof.

The term "biodegradable" includes that all or parts of the drug depot will degrade over time by the action of enzymes, by hydrolytic action and/or by other similar mechanisms in the human body. In various embodiments, "biodegradable" includes that the depot (e.g., microparticle, microsphere, etc.) can break down or degrade within the body to non-toxic components after or while a therapeutic agent has been or is being released. By "bioerodible" it is meant that the depot will erode or degrade over time due, at least in part, to contact with substances found in the surrounding tissue, fluids or by cellular action. By "bioabsorbable" it is meant that the depot will be broken down and absorbed within the human body, for example, by a cell or tissue. "Biocompatible" means that the depot will not cause substantial tissue irritation or necrosis at the target tissue site.

In some embodiments, the drug depot has pores that allow release of the drug from the depot. The drug depot will allow fluid in the depot to displace the drug. However, cell infiltration into the depot will be prevented by the size of the pores of the depot. In this way, in some embodiments, the depot should not function as a tissue scaffold and allow tissue growth. Rather, the drug depot will solely be utilized for drug delivery. In some embodiments, the pores in the drug depot will be less than 250 to 500 microns. This pore size will prevent cells from infiltrating the drug depot and laying down scaffolding cells. Thus, in this embodiment, drug will elute from the drug depot as fluid enters the drug depot, but cells will be prevented from entering. In some embodiments, where there are little or no pores, the drug will elute out from the drug depot by the action of enzymes, by hydrolytic action and/or by other similar mechanisms in the human body.

The phrases "sustained release" and "sustain release" (also referred to as extended release or controlled release) are used herein to refer to one or more therapeutic agent(s) that is introduced into the body of a human or other mammal and continuously or continually releases a stream of one or more therapeutic agents over a predetermined time period and at a therapeutic level sufficient to achieve a desired therapeutic effect throughout the predetermined time period. Reference to a continuous or continual release stream is intended to encompass release that occurs as the result of biodegradation in vivo of the drug depot, or a matrix or component thereof, or as the result of metabolic transformation or dissolution of the therapeutic agent(s) or conjugates of therapeutic agent(s).

The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug.

The two types of formulations (sustain release and immediate release) may be used in conjunction. The sustained release and immediate release may be in one or more of the same depots. In various embodiments, the sustained release and immediate release may be part of separate depots. For example a bolus or immediate release formulation of a capsaicinoid compound may be placed at or near the target site and a sustain release formulation may also be placed at or near the same site. Thus, even after the bolus becomes completely accessible, the sustain release formulation would continue to provide the active ingredient for the intended tissue.

In various embodiments, the drug depot can be designed to cause an initial burst dose of therapeutic agent within the first twenty-four to seventy-two hours after implantation. "Initial burst" or "burst effect" or "bolus dose" refers to the release of therapeutic agent from the depot during the first twenty-four hours to seventy-two hours after the depot comes in contact with an aqueous fluid (e.g., synovial fluid, cerebral spinal fluid, etc.). The "burst effect" is believed to be due to the increased release of therapeutic agent from the depot. In alternative embodiments, the depot (e.g., gel) is designed to avoid or reduce this initial burst effect (e.g., by applying an outer polymer coating to the depot). In some embodiments, the drug depot has a burst release surface that releases about 10%, 15%, 20%, 25%, 30%, 35%, 45%, to about 50% of the drug over 24 or 48 hours.

"Treating" or "treatment" of a disease or condition refers to executing a protocol that may include administering one or more drugs to a patient (human, other normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition. In addition, treating or treatment does not require complete alleviation of signs or symptoms, does not require a cure, and specifically includes protocols that have only a marginal effect on the patient. "Reducing pain and/or inflammation" includes a decrease in pain and/or inflammation and does not require complete alleviation of pain and/or inflammation signs or symptoms, and does not require a cure. In various embodiments, reducing pain and/or inflammation includes even a marginal decrease in pain and/or inflammation. By way of example, the administration of the effective dosage of the capsaicinoid compound may be used to prevent, treat or relieve the symptoms of pain and/or inflammation for different diseases or conditions. These disease/conditions may comprise oral-facial diseases, bursitis, tendonitis, chronic inflammatory diseases, including, but not limited to autoimmune diseases, such as multiple sclerosis, rheumatoid arthritis, osteoarthritis, insulin dependent diabetes (type I diabetes), systemic lupus erythrematosis and psoriasis, immune pathologies induced by infectious agents, such as helminthic (e.g., leishmaniasis) and certain viral infections, including HIV, and bacterial infections, including Lyme disease, tuberculosis and lepromatous leprosy, tissue transplant rejection, graft versus host disease and atopic conditions, such as asthma and allergy, including allergic rhinitis, gastrointestinal allergies, including food allergies, eosinophilia, conjunctivitis or glomerular nephritis. In some embodiments, the drug depot containing the therapeutic agent is not administered in, to or near the eye.

One chronic condition is sciatica. In general, sciatica is an example of pain that can transition from acute to neuropathic pain. Sciatica refers to pain associated with the sciatic nerve which runs from the lower part of the spinal cord (the lumbar region), down the back of the leg and to the foot. Sciatica generally begins with a herniated disc. The herniated disc itself leads to local immune system activation. The herniated disc also may damage the nerve root by pinching or compressing it, leading to additional immune system activation in the area. In various embodiments, the capsaicinoid compound may be used to reduce, treat, or prevent sciatic pain and/or inflammation by locally administering the capsaicinoid compound at one or more target tissue sites (e.g., nerve root, dorsal root ganglion, focal sites of pain, at or near the spinal column, etc.).

In some embodiments, the drug depot can be used to treat one or more target tissue sites that are involved in conditions/diseases, such as for example, rheumatoid arthritis, osteoarthritis, sciatica, carpal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, a surgical wound site or an incision site or the like. In some embodiments, the depot is not to be administered at or near the eye.

The term "implantable" as utilized herein refers to a biocompatible device (e.g., drug depot) retaining potential for successful placement within a mammal. The expression "implantable device" and expressions of the like import as utilized herein refers to an object implantable through surgery, injection, or other suitable means whose primary function is achieved either through its physical presence or mechanical properties.

"Localized" delivery includes delivery where one or more drugs are deposited within a tissue, for example, a nerve root of the nervous system or a region of the brain, or in close proximity (within about 0.1 cm, or preferably within about 10 cm, for example) thereto. For example, the drug dose delivered locally from the drug depot may be, for example, 10%, 20%, 30%, 40%, 50%, 60%, 70%, 80%, 90%, 95%, 99%, or 99.9% less than the oral dosage or injectable dose. In turn, systemic side effects, such as for example, liver transaminase elevations, hepatitis, liver failure, myopathy, constipation, etc. may be reduced or eliminated.

The term "mammal" refers to organisms from the taxonomy class "mammalian," including but not limited to humans, other primates such as chimpanzees, apes, orangutans and monkeys, rats, mice, cats, dogs, cows, horses, etc.

The phrase "pain management medication" includes one or more therapeutic agents that are administered to prevent, alleviate or remove pain entirely. These include anti-inflammatory agents, muscle relaxants, analgesics, anesthetics, narcotics, and so forth, and combinations thereof.

The phrase "release rate profile" refers to the percentage of active ingredient that is released over fixed units of time, e.g., mcg/hr, mcg/day, 10% per day for ten days, etc. As persons of ordinary skill know, a release rate profile may, but need not, be linear. By way of a non-limiting example, the drug depot may be a ribbon-like fiber that releases the capsaicinoid compound over a period of time.

The term "solid" is intended to mean a rigid material, while, "semi-solid" is intended to mean a material that has some degree of flexibility, thereby allowing the depot to bend and conform to the surrounding tissue requirements.

"Targeted delivery system" provides delivery of one or more drugs depots, gels or depots dispersed in the gel having a quantity of therapeutic agent that can be deposited at or near the target site as needed for treatment of pain, inflammation or other disease or condition.

The abbreviation "DLG" refers to poly(DL-lactide-co-glycolide).

The abbreviation "DL" refers to poly(DL-lactide).

The abbreviation "LG" refers to poly(L-lactide-co-glycolide).

The abbreviation "CL" refers to polycaprolactone.

The abbreviation "DLCL" refers to poly(DL-lactide-co-caprolactone).

The abbreviation "LCL" refers to poly(L-lactide-co-caprolactone).

The abbreviation "G" refers to polyglycolide.

The abbreviation "PEG" refers to poly(ethylene glycol).

The abbreviation "PLGA" refers to poly(lactide-co-glycolide) also known as poly(lactic-co-glycolic acid), which are used interchangeably.

The abbreviation "PLA" refers to polylactide.

The abbreviation "POE" refers to poly(orthoester).

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

TRPV1 Compounds

The transient receptor potential cation channel subfamily V member 1 (TRPV1), also known as the capsaicin receptor and the vanilloid receptor 1, is a protein that, in humans, is encoded by the TRPV1 gene. The vanilloid receptor TRPV1 is a homotetrameric, non-selective cation channel abundantly expressed in the nociceptors (c-fibers). See Caterina M J, Schumacher M A, Tominaga M, Rosen T A, Levine J D, Julius D (October 1997). "The capsaicin receptor: a heat-activated ion channel in the pain pathway". Nature 389 (6653): 816-24. and Xue Q, Yu Y, Trilk S L, Jong B E, Schumacher M A (August 2001). "The genomic organization of the gene encoding the vanilloid receptor: evidence for multiple splice variants". Genomics 76 (1-3): 14-20. The function of TRPV1 is detection and regulation of body temperature. Additionally, TRPV1 provides sensation of heat and pain. TRPV1 compounds include those compounds that agonize and/or antagonize the TRPV1 receptor. When TRPV1 is activated by agonists such as capsaicin and other factors such as heat and acidosis, calcium enters the cell and pain signals are initiated. After disease or injury, cutaneous nociceptors may become persistently hyperactive, spontaneously transmitting excessive pain signals to the spinal cord in the absence of painful stimuli, resulting in various types of chronic pain. When TRPV1 is continuously activated through prolonged exposure to an agonist (e.g., capsaicin), excessive calcium enters the nerve fiber, initiating processes that result in long-term yet reversible impairment of nociceptor function. This is believed to be the mechanism by which application of capsaicin provides relief from pain.

Some examples of TRPV1 compounds include TRPV1 agonists and antagonists. Some TRPV1 agonists useful in the present application include capsaicin, capsaicin analogs and derivatives, and other low molecular weight compounds (i.e., MW<1000) that agonize the TRPV1. In addition to capsaicin, a variety of capsaicin analogs and derivatives, and other TRPV1 agonists may be administered. Vanilloids, such as capsaicinoids, are an example of useful TRPV1 agonists. Exemplary vanilloids for use according to the invention include N-vanillyl-alkaneclienamides, N-vanillyl-alkanedienyls, N-vanillyl-cis-monounsaturated alkenamides, capsaicin, dihydrocapsaicin, norhydrocapsaicin, nordihydrocapsaicin, homocapsaicin, and homodihydrocapsaicin. In another embodiment, the TRPV1 agonist is a compound lacking the vanillyl function, such as piperine or a dialdehyde sesquiterpene (for example warburganal, polygodial, or isovelleral). In another embodiment, the TRPV1 agonist is a triprenyl phenol, such as scutigeral. Additional exemplary TRPV1 agonists are described in U.S. Pat. Nos. 4,599,342; 5,962,532; 5,762,963; 5,221,692; 4,313,958; 4,532,139; 4,544,668; 4,564,633; 4,544,669; 4,493,848; 4,532,139; 4,564,633; and 4,544,668; and PCT publication WO 00/50387. Other useful TRPV1 agonists include pharmacologically active gingerols, piperines, shogaols, and more specifically guaiacol, eugenol, zingerone, civamide, nonivamide, nuvanil, olvanil, NE-19550, NE-21610, and NE-28345 (see Dray et al., 1990, Eur. J. Pharmacol 181:289-93 and Brand et al., 1990, Agents Actions 31:329-40), olvanil, resiniferatoxin, resiniferatoxin analogs, and resiniferatoxin derivatives (e.g., tinyatoxin). Any active geometric- or stereo-isomer of the forgoing agonists may be used.

Other TRPV1 agonists are vanilloids that have TRVP1 receptor-binding moieties such as mono-phenolic mono-substituted benzylamine amidated with an aliphatic cyclized, normal or branched substitution. Still other useful TRPV1 agonists for practicing the invention can be readily identified using standard methodology, such as that described in U.S. patent publication US20030104085. Useful assays for identification of TRPV1 agonists include, without limitation, receptor binding assays; functional assessments of stimulation of calcium influx or membrane potential in cells expressing the TRPV1 receptor, assays for the ability to induce cell death in such cells (e.g., selective ablation of C-fiber neurons), and other assays known in the art Mixtures of agonists and pharmaceutically acceptable salts of any of the foregoing may also be used. See Szallasi and Blumberg, 1999, Pharmacological Reviews 51:159-211, U.S. Pat. No. 5,879,696, and references therein.

TRPV1 include TRPV1 antagonists. The term "TRPV1 antagonist" and "TRPV1 inhibitor" includes any agent that can inhibit the activity of TRPV1 (i.e. block TRPV1-mediated signaling cascade) at an ophthalmically relevant concentration. TRPV1 antagonists useful in the methods of the invention include, but are not limited to, fused azabicyclic, heterocyclic, and amide compounds as described, for example, in U.S. Patent Application No. 2004/0157849, U.S. Patent Application No. 2004/0209884, U.S. Patent Application No. 2005/0113576, International Patent Application No. WO 05/016890, U.S. Patent Application No. 2004/0254188, U.S. Patent Application No. 2005/0043351, International Patent Application No. WO 05/040121, U.S. Patent Application No. 2005/0085512, and Gomtsyan et al., 2005, J. Med. Chem. 48:744-752; fused pyridine derivatives as described, for example, in U.S. Patent Application No. 2004/0138454; pyridyl piperazinyl ureas as described, for example, in Swanson et al., 2005, J. Med. Chem. 48:1857-1872 and U.S. Patent Application No. 2005/0049241, as well as AMG8163 (Bannon et al., 2005, 11.sup.th World Congress on Pain) and BCTC (Sun et al., 2003, Chem. Lett. 13:3611-3616); 2-(piperazine-1-yl)-1H-Benzimidazole; pyridazinylpiperazines; urea derivatives as describe, for example, in U.S. Patent Application No. 2005/0107388, U.S. Patent Application No. 2005/0187291, and U.S. Patent Application No. 2005/0154230, as well as A-425619 (El Kouhen et al., 2005, J. Pharmacol. Exp. Ther. 314:400-409); cinnamides, including SB-366791 (Gunthorpe et al., 2004, Neuropharmacology 46:133-149) and AMG 9810 (Gavva et al., 2005, J. Pharmacol. Exp. Ther. 313:474-484); each of which is incorporated by reference. Particular TRPV1 antagonists useful in the methods of the invention include AMG-517 and AMG-628 (Amgen Inc., Thousand Oaks, Calif.). TRPV1 antagonists useful in the present application are also described, for example, in International Patent Application No. WO 2006065484; International Patent Application No. WO 2003070247; U.S. Patent Application No. US 2005080095; and International Patent Application No. WO 2005007642. These disclosures are herein incorporated by reference.

Capsaicinoid Compounds

Capsaicin belongs to the family of compounds known as capsaicinoids. Capsaicinoid compounds include, but are not limited to, capsaicin, nordihydrocapsaicin, dihydrocapsaicin, homodihydrocapsaicin, homocapsaicin, nonivamide, and pro-capsaicinoid compounds including prodrugs thereof. Capsaicinoid prodrugs (e.g., capsaicin prodrugs) are compounds that are administered in an inactive form that is metabolized in the body in vivo into the active compound. This optimizes targeted drug delivery.

In general, capsaicin comprises N-(4-hydroxy-3-methoxybenzyl)-8-methylnon-trans-6-enamide. Capsaicin can be derived from plants of the solanaceae family (e.g., hot chili peppers). Capsaicin can be readily obtained by ethanol extraction of the fruit of capsicum frutescens or capsicum annum. Capsaicin is available commercially as Capsaicin USP from Steve Weiss & Co., 315 East 68th Street, New York, N.Y. 10021 and can also be prepared synthetically by published methods. See Michalska et al., "Synthesis and Local Anesthetic Properties of N-substituted 3,4-Dimethoxyphenethylamine Derivatives", Diss Pharm. Pharmacol., Vol. 24, (1972), pp. 17-25, (Chem. Abs. 77: 19271a), discloses N-Pentyl and N-hexyl 3,4-dimethoxyphenylacetamides which are reduced to the respective secondary amines.

Capsaicin (USP) contains not less than 10% total capsaicinoids, which typically corresponds to 63% pure capsaicin. USP capsaicin is trans-capsaicin (55-60%) and also contains the precursors dihydrocapsaicin and nordihydrocapsaicin. These types of capsaicin compounds can be used in the drug depot.

Capsaicinoid mediated effects include: (i) activation of nociceptors in peripheral tissues; (ii) eventual desensitization of peripheral nociceptors to one or more stimulus modalities; (iii) cellular degeneration of sensitive A-delta and C-fiber afferents; (iv) activation of neuronal proteases; (v) blockage of axonal transport; and (vi) the decrease of the absolute number of nociceptive fibers without affecting the number of non-nociceptive fibers.

When referring to a capsaicinoid compound or prodrug thereof, unless otherwise specified or apparent from context it is understood that the inventors are also referring to pharmaceutically acceptable salts. One well-known commercially available salt for capsaicinoid is its hydrochloride salt. Some other examples of potentially pharmaceutically acceptable salts include those salt-forming acids and bases that do not substantially increase the toxicity of a compound, such as, salts of alkali metals such as magnesium, potassium and ammonium, salts of mineral acids such as hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, and the like.

Further, when referring to the capsaicinoid compound the active ingredient may not only be in the salt form, but also in the base form (e.g., free base). In various embodiments, if it is in the base form, it may be combined with polymers under conditions in which there is not severe polymer degradation, as may be seen upon heat or solvent processing that may occur with PLGA or PLA. By way of a non limiting example, when formulating the capsaicinoid compound with poly (orthoesters) it may be desirable to use the capsaicinoid compound base formulation. By contrast, when formulating the capsaicinoid compound with PLGA, it may be desirable to use the HCl salt form. In some embodiments, the capsaicinoid compound may be incorporated into a polymer core with a polymer and then coated with the same or different polymer.

Pharmaceutically acceptable salts of the capsaicinoid compound include salts prepared from pharmaceutically acceptable non-toxic bases or acids including inorganic or organic bases, inorganic or organic acids and fatty acids. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethyl amine, tripropylamine, tromethamine, and the like. When the compound of the current application is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Fatty acid salts may also be used, e.g., fatty acid salts having greater than 2 carbons, greater than 8 carbons or greater than 16 carbons, such as butyric, caprioc, caprylic, capric, lauric, mystiric, palmitic, stearic, arachidic or the like.

In some embodiments, in order to reduce the solubility of the capsaicinoid compound to assist in obtaining a controlled release depot effect, the capsaicinoid compound is utilized as the free base or utilized in a salt, which has relatively lower solubility. For example, the present application can utilize an insoluble salt such as a fatty acid salt. Representative fatty acid salts include salts of oleic acid or linoleic acid. In preferred embodiments fatty acid salts with between 8 to 20 carbons are used to produce salts with low solubility, such as capsaicinoid palmeate and capsaicinoid stearate. Most preferably, fatty acid salts with between 12 to 18 carbons are used. Other embodiments can utilize a lipid soluble salt of capsaicinoid.

Suitable drug compound depots for use in the present application are described in U.S. Ser. No. 12/420,197, filed Apr. 8, 2009 and published as US20090264490. The entire disclosure is herein incorporated by reference.

In some embodiments, the TRPV1 compound (e.g., capsaicinoid compound) is released locally from the device at a dose of from about 0.3 mg/day or about 1.8 mg/day or about 3.6 mg/day to about 180 mg/day or about 360 mg/day. In some embodiments, the TRPV1 compound (e.g., capsaicinoid compound) is released from the device at a dose of 0.75 mg to 16 mg per day. In some embodiments, the TRPV1 compound (e.g., capsaicinoid compound) can be released locally at a dose of from about 0.5 mg/day to about 15 mg/day.

In some embodiments, the initial burst or bolus release is about 2 to 20 times higher from 1 hour to about two weeks than the sustained release daily dose released from the device. In some embodiments, the capsaicinoid compounds can have a burst release in 24 to 48 hours.

In some embodiments, the TRPV1 compound (e.g., capsaicinoid compound) is in the depot with a GABA compound where the GABA compound comprises gabapentin, which is released from the device at a dosage of from about 0.3 mg or 1 mg to about 8 mg, 10 mg, 16 mg or 32 mg per day. In some embodiments, the TRPV1 compound (e.g., capsaicinoid compound) is released from the device at a dosage of from about 0.1 mg or 0.3 mg to about 1 mg, 3 mg, 5 mg or 10 mg per day. In some embodiments, the TRPV1 compound (e.g., capsaicinoid compound) can be released from the depot at a dose of 0.002 mg to 16 mg per day.

In some embodiments, the ratio of gabapentin to the TRPV1 compound (e.g., capsaicinoid compound) would be 300:1. For pregabalin, the ratio would be approximately 100:1. In some embodiments, the drug depot releases 300 mg of pregabalin per day.

In some embodiments, the drug depot comprises a TRPV1 compound (e.g., capsaicinoid compound) that is in the drug depot in an amount of from about 0.1% to about 75% by weight.

In some embodiments, the drug depot comprises both a capsaicinoid compound and a capsaicinoid prodrug in a single formulation. In some embodiments, the capsaicinoid prodrug can be in a separate depot from the capsaicinoid compound.

In some embodiments, a capsaicinoid compound, a steroid, bupivacaine, and/or lidocaine can be administered in an immediate release or sustained release liquid by injection before, after, or during the administration of the capsaicinoid compound depot.

The capsaicinoid compound or its pharmaceutically acceptable salt may be administered with a muscle relaxant. Exemplary muscle relaxants include by way of example and not limitation, alcuronium chloride, atracurium bescylate, carbamate, carbolonium, carisoprodol, chlorphenesin, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, or combinations thereof.

The drug depot may comprise other therapeutic agents in addition to the capsaicinoid compound as well. These therapeutic agents, in various embodiments, block the transcription or translation of TNF-α or other proteins in the inflammation cascade. Suitable therapeutic agents include, but are not limited to, integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibodies (daclizumab, basilicimab), ABX (anti IL-8 antibodies), recombinant human IL-10, or HuMax IL-15 (anti-IL 15 antibodies).

Other suitable therapeutic agents include IL-1 inhibitors, such Kineret® (anakinra) which is a recombinant, non-glycosylated form of the human inerleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogs (which reduce TNF-α production by macrophages), bone morphogenetic protein (BMP) type 2 and BMP-4 (inhibitors of caspase 8, a TNF-α activator), quinapril (an inhibitor of angiotensin II, which upregulates TNF-α), interferons such as IL-11 (which modulate TNF-α receptor expression), and aurin-tricarboxylic acid (which inhibits TNF-α), may also be useful as therapeutic agents for reducing inflammation. It is further contemplated that where desirable a pegylated form of the above may be used. Examples of still other therapeutic agents include NF kappa B inhibitors such as glucocorticoids, antioxidants, such as dithiocarbamate, and other compounds, such as, for example, sulfasalazine.

Examples of therapeutic agents suitable for use also include, but are not limited to an anti-inflammatory agent, an analgesic agent, or an osteoinductive growth factor or a combination thereof. Anti-inflammatory agents include, but are not limited to, apazone, celecoxib, diclofenac, diflunisal, enolic acids (piroxicam, meloxicam), etodolac, fenamates (mefenamic acid, meclofenamic acid), gold, ibuprofen, indomethacin, ketoprofen, ketorolac, nabumetone, naproxen, nimesulide, salicylates, sulfasalazine [2-hydroxy-5-[-4-[C2-pyridinylamino)sulfonyl]azo]benzoic acid, sulindac, tepoxalin or tolmetin; as well as antioxidants, such as dithiocarbamate, steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable anabolic growth or anti-catabolic growth factors include, but are not limited to, a bone morphogenetic protein, a growth differentiation factor (e.g., GDF-5), a LIM mineralization protein, CDMP or progenitor cells or a combination thereof.

Suitable analgesic agents include, but are not limited to, acetaminophen, bupivacaine, lidocaine, gamma-aminobutyric acid (GABA), clonidine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papavereturn, pentazocine, pethidine, phenoperidine, piritramide, dextropropoxyphene, remifentanil, tilidine, tramadol, codeine, dihydrocodeine, meptazinol, dezocine, eptazocine, flupirtine, amitriptyline, carbamazepine, gabapentin, pregabalin, or a combination thereof.

The therapeutic agent in the device may include, but is not limited to, members of the fibroblast growth factor family, including acidic and basic fibroblast growth factor (FGF-1 and FGF-2) and FGF-4, members of the platelet-derived growth factor (PDGF) family, including PDGF-AB, PDGF-BB and PDGF-AA; EGFs; the TGF-β superfamily, including TGF-β1, 2 or 3; osteoid-inducing factor (OIF); angiogenin(s); endothelins; hepatocyte growth factor or keratinocyte growth factor; members of the bone morphogenetic proteins (BMP's) BMP-1, BMP-3, BMP-2; OP-1, BMP-2A, BMP-2B, or BMP-7; HBGF-1 or HBGF-2; growth differentiation factors (GDF's); members of the hedgehog family of proteins, including indian, sonic and desert hedgehog; ADMP-1; other members of the interleukin (IL) family; or members of the colony-stimulating factor (CSF) family, including CSF-1, G-CSF, and GM-CSF, or isoforms thereof; or VEGF, NELL-1 (neural epidermal growth factor-like 1), CD-RAP (cartilage-derived retinoic acid-sensitive protein) or combinations thereof.

In some embodiments, the device comprises osteogenic proteins. Exemplary osteogenic proteins include, but are not limited to, OP-1, OP-2, OP-3, BMP-2, BMP-3, BMP-3b, BMP-4, BMP-5, BMP-6, BMP-9, BMP-10, BMP-11, BMP-12, BMP-13, BMP-14, BMP-15, GDF-1, GDF-2, GDF-3, GDF-5, GDF-6, GDF-7, GDF-8, GDF-9, GDF-10, GDF-11, GDF-12, CDMP-1, CDMP-2, CDMP-3, DPP, Vg-1, Vgr-1, 60A protein, NODAL, UNIVIN, SCREW, ADMP, NEURAL, and TGF-beta. As used herein, the terms "morphogen," "bone morphogen," "BMP," "osteogenic protein" and "osteogenic factor" embrace the class of proteins typified by human osteogenic protein 1 (hOP-1).

Exemplary growth factors include, but are not limited to, members of the transforming growth factor beta family, including bone morphogenetic protein 2 (BMP-2); bone morphogenetic protein 4 (BMP-4); and transforming growth factors beta-1, beta-2, and beta-3 (potent keratinocyte growth factors). Other useful members of the transforming growth factor beta family include BMP-3, BMP-5, BMP-6, BMP-9, DPP, Vgl, Vgr, 60A protein, GDF-1, GDF-3, GDF-5, GDF-6, GDF-7, CDMP-1, CDMP-2, CDMP-3, BMP-10, BMP-11, BMP-13, BMP-15, Univin, Nodal, Screw, ADMP, Neural, and amino acid sequence variants thereof. Other growth factors include epidermal growth factor (EGF), which induces proliferation of both mesodermal and ectodermal cells, particularly keratinocytes and fibroblasts; platelet-derived growth factor (PDGF), which exerts proliferative effects on mesenchymal cells; fibroblast growth factor (FGF), both acidic and basic; and insulin-like growth factor 1 (IGF-1) or 2 (IGF-2), which mediate the response to growth hormone, particularly in bone growth. Further growth factors include osteogenic proteins. A particularly preferred osteogenic protein is OP-1, also known as bone morphogenetic protein 7 (BMP-7). OP-1 is a member of the transforming growth factor beta gene superfamily.

The capsaicinoid compound may also be administered with non-active ingredients. These non-active ingredients may have multi-functional purposes including the carrying, stabilizing and controlling the release of the therapeutic agent(s). The sustained release process, for example, may be by a solution-diffusion mechanism or it may be governed by an erosion-sustained process. Typically, the depot will be a solid or semi-solid formulation comprised of a biocompatible material that can be biodegradable.

Exemplary excipients that may be formulated with the capsaicinoid compound in addition to the biodegradable polymer include but are not limited to MgO (e.g., 1 wt. %), 5050 DLG 1A (Evonik Degussa Corporation, Birmingham Laboratories Birmingham, Ala.), mPEG, propylene glycol, mannitol, trehalose, TBO-Ac, mPEG, Span-65, Span-85, pluronic F127, TBO-Ac, sorbitol, cyclodextrin, maltodextrin, pluronic F68, CaCl, dextran, ascorbic acid, tocopherols, methionine or combinations thereof. In some embodiments, the excipients comprise from about 0.001 wt. % to about 50 wt. % of the formulation. In some embodiments, the excipients comprise from about 0.001 wt. % to about 40 wt. % of the formulation. In some embodiments, the excipients comprise from about 0.001 wt. % to about 30 wt. % of the formulation. In some embodiments, the excipients comprise from about 0.001 wt. % to about 20 wt. % of the formulation. In some embodiments, the excipients comprise from about 0.001 wt. % to about 10 wt. % of the formulation. In some embodiments, the excipients comprise from about 0.001 wt. % to about 5 wt. % of the formulation. In some embodiments, the excipients comprise from about 0.001 wt. % to about 2 wt. % of the formulation.

In various embodiments, the non-active ingredients will be durable within the tissue site for a period of time equal to or greater than (for biodegradable components) or greater than (for non-biodegradable components) the planned period of drug delivery.

In some embodiments, the depot material may have a melting point or glass transition temperature close to or higher than body temperature, but lower than the decomposition or degradation temperature of the therapeutic agent. However, the pre-determined erosion of the depot material can also be used to provide for slow release of the loaded therapeutic agent(s). Non-biodegradable polymers include but are not limited to PVC and polyurethane. In some embodiments, a plasticizer is used to lower glass translation temperature in order to affect stability of the drug depot.

In some embodiments, the polymer can be in powdered form having a particle size predominantly in a range from about 3.5 to about 10 micrometers that can be reconstituted for delivery.

In various embodiments, the drug depot comprises a capsaicinoid compound, bupivacaine or lidocaine and a biodegradable polymer in amorphous, crystalline or semicrystalline form; where the crystalline form may include polymorphs, solvates or hydrates.

In some embodiments, the TRPV1 compound (e.g., capsaicinoid compound) can be in powdered form having a particle sizes predominantly in a range from about 3.5 to about 10 micrometers that can be reconstituted for delivery.

In some embodiments, the drug depot has a modulus of elasticity in the range of about $1\times10^1$ to about $6\times10^5$ dyn/cm$^2$, or $2\times10^4$ to about $5\times10^5$ dyn/cm$^2$, or $5\times10^4$ to about $5\times10^5$ dyn/cm². In some embodiments, the drug depot is in the form of a solid. In some embodiments, the drug depot comprises a capsaicinoid compound, bupivacaine or lidocaine.

In some embodiments, the capsaicinoid compound, bupivacaine, and/or lidocaine is administered in a depot that is solid or in semi-solid form. The solid or semi-solid form of the depot may have a pre-dosed viscosity in the range of about 1 to about 2000 centipoise (cps), 1 to about 200 cps, or 1 to about 100 cps. After the solid or semi-solid depot is administered to the target site, the viscosity of the semi-solid or solid depot will increase and the semi-solid will have a modulus of elasticity in the range of about $1 \times -10^2$ to about $6 \times 10^5$ dynes/cm², or $2 \times 10^4$ to about $5 \times 10^5$ dynes/cm², or $5 \times 10^4$ to about $5 \times 10^5$ dynes/cm².

In various embodiments, the semi-solid or solid depot may comprise a polymer having a molecular weight, as shown by the inherent viscosity, from about 0.10 dL/g to about 1.2 dL/g or from about 0.10 dL/g to about 0.50 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.55 dL/g, about 0.50 to about 0.70 dL/g, about 0.55 to about 0.6 dL/g, about 0.60 to about 0.80 dL/g, about 0.70 to about 0.90 dL/g, about 0.80 to about 1.00 dL/g, about 0.90 to about 1.10 dL/g, about 1.0 to about 1.2 dL/g, about 1.1 to about 1.3 dL/g, about 1.2 to about 1.4 dL/g, about 1.3 to about 1.5 dL/g, about 1.4 to about 1.6 dL/g, about 1.5 to about 1.7 dL/g, about 1.6 to about 1.8 dL/g, about 1.7 to about 1.9 dL/g, or about 1.8 to about 2.1 dL/g.

In some embodiments, the drug depot may not be fully biodegradable. For example, the drug depot may comprise polyurethane, polyurea, polyether(amides) (PEAs), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics, methacrylates, poly (N-isopropylacrylamide), PEO-PPO-PEO (pluronics) or combinations thereof. Typically, these types of drug depots may need to be removed after a certain amount of time.

In some instances, it may be desirable to avoid having to remove the drug depot after use. In those instances, the depot may comprise a biodegradable material. There are numerous materials available for this purpose and having the characteristic of being able to breakdown or disintegrate over a prolonged period of time when positioned at or near the target tissue. As a function of the chemistry of the biodegradable material, the mechanism of the degradation process can be hydrolytical or enzymatical in nature, or both. In various embodiments, the degradation can occur either at the surface (heterogeneous or surface erosion) or uniformly throughout the drug delivery system depot (homogeneous or bulk erosion).

In various embodiments, the depot may comprise a bioerodible, a bioabsorbable, and/or a biodegradable biopolymer that may provide immediate release, or sustained release of the casaicin compound. Examples of suitable sustained release biopolymers include but are not limited to poly (alpha-hydroxy acids), poly (lactide-co-glycolide) (PLGA), polylactide (PLA), polyglycolide (PG), polyethylene glycol (PEG) conjugates of poly (alpha-hydroxy acids), poly (orthoester)s (POE), polyaspirins, polyphosphagenes, polyester amides (PEAs), collagen, starch, pre-gelatinized starch, hyaluronic acid, chitosans, gelatin, alginates, albumin, fibrin, vitamin E compounds, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof.

In some embodiments, the PEA comprises a diacid, a diol and at least one amino acid. The diacid is can be a C2 to C12 diacid and can be either aliphatic or unsaturated. The diol can be C2 to C12 and may include branching and unsaturation. A triol such as glycerol may also be added to the formulation to induce mild crosslinking in an embodiment where the formulation has a low solid percentage. The first amino acid may be glycine, valine, alanine, leucine, isoleucine or phenylalanine. An optional second amino acid may also be included that may contain a reactive side group for the attachment of pharmacologically active compounds or property modifiers. The second amino acid may be lysine, tyrosine, glutamic acid, or cysteine. This PEA family may also contain an optional hydrophilic diol or diamine for property modification. This component may be in the polymer backbone or attached as a pendant group. This optional diol or diamine may be, for example, polyethylene glycol (PEG), polypropyleneglycol (PPG), polyvinylpyrrolidone (PVP), hydroxyethylmethacrylate (HEMA), or hyaluronic acid.

As persons of ordinary skill are aware, mPEG and/or PEG may be used as a plasticizer for PLGA, but other polymers/excipients may be used to achieve the same effect. mPEG imparts malleability to the resulting formulations. In some embodiments, these biopolymers may also be coated on the drug depot to provide the desired release profile. In some embodiments, the coating thickness may be thin, for example, from about 5, 10, 15, 20, 25, 30, 35, 40, 45 or 50 microns to thicker coatings 60, 65, 70, 75, 80, 85, 90, 95, 100 microns to delay release of the drug from the depot. In some embodiments, the range of the coating on the drug depot ranges from about 5 microns to about 250 microns or 5 microns to about 200 microns to delay release from the drug depot.

In various embodiments, the drug depot comprises poly (lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone, L-lactide-co-ε-caprolactone or a combination thereof. In some embodiments, the drug depot comprises one or more polymers (e.g., poly-D-lactide, caprolactone, etc.) having an inherent viscosity of 0.6 to about 1.0 dL/gm and a MW of 50,000 to about 125,000 Da.

In some embodiments, the drug depot comprises one or more polymers (e.g., PLA, PLGA, etc.) having a MW of from about 15,000 to about 150,000 Da or from about 25,000 to about 100,000 Da.

As persons of ordinary skill in the art are aware, an implantable depot compositions having a blend of polymers with different end groups are used the resulting formulation will have a lower burst index and a regulated duration of delivery. For example, one may use polymers with acid (e.g., carboxylic acid) and ester end groups (e.g., methyl or ethyl ester end groups).

Additionally, by varying the comonomer ratio of the various monomers that form a polymer (e.g., the L/G (lactic acid/glycolic acid) or G/CL (glycolic acid/polycaprolactone) ratio for a given polymer) there will be a resulting depot composition having a regulated burst index and duration of delivery. For example, a depot composition having a polymer with a L/G ratio of 50:50 may have a short duration of delivery ranging from about two days to about one month; a depot composition having a polymer with a L/G ratio of 65:35 may have a duration of delivery of about two months; a depot composition having a polymer with a L/G ratio of 75:25 or L/CL ratio of 75:25 may have a duration of delivery of about three months to about four months; a depot composition having a polymer ratio with a L/G ratio of 85:15 may have a duration of delivery of about five months; a depot composition having a polymer with a L/CL ratio of 25:75 or PLA may have a duration of delivery greater than or equal to six months; a depot composition having a terpolymer of CL/G/L with G greater than 50% and L greater than 10% may have a duration of delivery of about one month and a depot composition having a terpolymer of CL/G/L with G less than 50% and L less than 10% may have a duration months up to six months. In general, increasing the G content relative to the CL content shortens the duration of delivery whereas increasing the CL content relative to the G content lengthens the duration of delivery. Thus, among other things, depot compositions having a blend of polymers having different molecular weights, end groups and comonomer ratios can be used to create a depot formulation having a lower initial burst and a regulated duration of delivery.

The depot may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfate, sodium bisulfite, sodium thiosulfate, thimerosal, methylparaben, polyvinyl alcohol and phenylethyl alcohol; solubility adjusting agents; stabilizers; and/or cohesion modifiers. If the depot is to be placed in the spinal area, in various embodiments, the depot may comprise sterile preservative free material.

The depot can be different sizes, shapes and configurations. There are several factors that can be taken into consideration in determining the size, shape and configuration of the drug depot. For example, both the size and shape may allow for ease in positioning the drug depot at the target tissue site that is selected as the implantation or injection site. In addition, the shape and size of the system should be selected so as to minimize or prevent the drug depot from moving after implantation or injection. In various embodiments, the drug depot can be shaped like a sphere, a cylinder such as a rod or fiber, a flat surface such as a disc, film or sheet (e.g., ribbon-like) or the like. Flexibility may be a consideration so as to facilitate placement of the drug depot. In various embodiments, the drug depot can be different sizes, for example, the drug depot may be a length of from about 0.5 mm to 5 mm and have a diameter of from about 0.01 to about 4 mm. In various embodiments, as the diameter decreases, the surface area that comes in contact with the bodily fluid of the depot increases and therefore release of the drug from the depot increases. In various embodiments, the drug depot may have a layer thickness of from about 0.005 to 1.0 mm, such as, for example, from 0.05 to 0.75 mm.

Radiographic markers can be included on the drug depot to permit the user to position the depot accurately into the target site of the patient. These radiographic markers will also permit the user to track movement and degradation of the depot at the site over time. In this embodiment, the user may accurately position the depot in the site using any of the numerous diagnostic imaging procedures. Such diagnostic imaging procedures include, for example, X-ray imaging or fluoroscopy. Examples of such radiographic markers include, but are not limited to, barium, calcium phosphate, bismuth, iodine, tantalum, tungsten, and/or metal beads or particles. In various embodiments, the radiographic marker could be a spherical shape or a ring around the depot.

Drug Depot in Matrix Form

The matrix provides a scaffold to release TRPV1 compound (e.g., capsaicinoid compound) in vivo in three dimensions. In some embodiments, one or more tissue matrices are stacked on one another.

In some embodiments, the matrix comprises a plurality of pores. In some embodiments, at least 10% of the pores are between about 10 micrometers and about 500 micrometers at their widest points. In some embodiments, at least 20% of the pores are between about 50 micrometers and about 150 micrometers at their widest points. In some embodiments, at least 30% of the pores are between about 30 micrometers and about 70 micrometers at their widest points. In some embodiments, at least 50% of the pores are between about 10 micrometers and about 500 micrometers at their widest points. In some embodiments, at least 90% of the pores are between about 50 micrometers and about 150 micrometers at their widest points. In some embodiments, at least 95% of the pores are between about 100 micrometers and about 250 micrometers at their widest points. In some embodiments, 100% of the pores are between about 10 micrometers and about 300 micrometers at their widest points.

In some embodiments, the matrix has a porosity of at least about 30%, at least about 50%, at least about 60%, at least about 70%, at least about 90%. The pore enhance release of the capsaicinoid compound and may support ingrowth of cells, formation or remodeling of bone, cartilage and/or vascular tissue.

In some embodiments, the matrix may comprise natural and/or synthetic material. For example, the tissue scaffold may comprise poly (alpha-hydroxy acids), poly (lactide-co-glycolide) (PLGA), polylactide (PLA), polyglycolide (PG), polyethylene glycol (PEG) conjugates of poly (alpha-hydroxy acids), polyorthoesters (POE), polyaspirins, polyphosphagenes, PEAs, collagen, hydrolyzed collagen, gelatin, hydrolyzed gelatin, fractions of hydrolyzed gelatin, elastin, starch, pre-gelatinized starch, hyaluronic acid, chitosan, alginate, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate), polydioxanone, methylmethacrylate (MMA), MMA and N-vinylpyyrolidone, polyamide, oxycellulose, copolymer of glycolic acid and trimethylene carbonate, polyesteramides, polyetheretherketone, polymethylmethacrylate, silicone, hyaluronic acid, chitosan, or combinations thereof.

In some embodiments, the matrix comprises collagen. Exemplary collagens include human or non-human (bovine, ovine, and/or porcine), as well as recombinant collagen or combinations thereof. Examples of suitable collagen include, but are not limited to, human collagen type I, human collagen type II, human collagen type III, human collagen type IV, human collagen type V, human collagen type VI, human collagen type VII, human collagen type VIII, human collagen type IX, human collagen type X, human collagen type XI, human collagen type XII, human collagen type XIII, human collagen type XIV, human collagen type XV, human collagen type XVI, human collagen type XVII, human collagen type XVIII, human collagen type XIX, human collagen type XXI, human collagen type XXII, human collagen type XXIII, human collagen type XXIV, human collagen type XXV, human collagen type XXVI, human collagen type XXVII, and human collagen type XXVIII, or combinations thereof. Collagen further may comprise hetero- and homo-trimers of any of the above-recited collagen types. In some embodiments, the collagen comprises hetero- or homo-trimers of human collagen type I, human collagen type II, human collagen type III, or combinations thereof.

In some embodiments, the matrix comprises collagen-containing biomaterials from the implant market which, when placed in a bone defect, provide scaffolding around which the patient's new bone will grow, gradually replacing the carrier matrix as the target site heals. Examples of suitable carrier matrices may include, but are not limited to, the Master-Graft® Matrix produced by Medtronic Sofamor Danek, Inc., Memphis, Tenn.; MasterGraft® Putty produced by Medtronic Sofamor Danek, Inc., Memphis, Tenn.; Absorbable Collagen Sponge ("ACS") produced by Integra LifeSciences Corporation, Plainsboro, N.J.; bovine skin collagen fibers coated with hydroxyapatite, e.g. Healos®. marketed by Johnson & Johnson, USA; collagen sponges, e.g. Hemostagene® marketed by Coletica S A, France, or e.g. Helisat® marketed by Integra Life Sciences Inc., USA; and Collagraft® Bone Graft Matrix produced by Zimmer Holdings, Inc., Warsaw, Ind.

In some embodiments, the embodiments the matrix may comprise particles of bone-derived materials. The bone-derived material may include one or more of non-demineralized bone particles, demineralized bone particles, lightly demineralized bone particles, and/or deorganified bone particles.

In some embodiments, the matrix may be seeded with harvested bone cells and/or bone tissue, such as for example, cortical bone, autogenous bone, allogenic bones and/or xenogenic bone. In some embodiments, the matrix may be seeded with harvested cartilage cells and/or cartilage tissue (e.g., autogenous, allogenic, and/or xenogenic cartilage tissue). For example, before insertion into the target tissue site, the matrix can be wetted with the graft bone tissue/cells, usually with bone tissue/cells aspirated from the patient, at a ratio of about 3:1, 2:1, 1:1, 1:3 or 1:2 by volume. The bone tissue/cells are permitted to soak into the matrix provided, and the matrix may be kneaded by hand or machine, thereby obtaining a pliable consistency that may subsequently be packed into the bone defect. In some embodiments, the matrix provides a malleable, non-water soluble carrier that permits accurate placement and retention at the implantation site.

The matrix may contain an inorganic material, such as an inorganic ceramic and/or bone substitute material. Exemplary inorganic materials or bone substitute materials include but are not limited to aragonite, dahlite, calcite, amorphous calcium carbonate, vaterite, weddellite, whewellite, struvite, urate, ferrihydrate, francolite, monohydrocalcite, magnetite, goethite, dentin, calcium carbonate, calcium sulfate, calcium phosphosilicate, sodium phosphate, calcium aluminate, calcium phosphate, hydroxyapatite, alpha-tricalcium phosphate, dicalcium phosphate, β-tricalcium phosphate, tetracalcium phosphate, amorphous calcium phosphate, octacalcium phosphate, BIOGLASS™, fluoroapatite, chlorapatite, magnesium-substituted tricalcium phosphate, carbonate hydroxyapatite, substituted forms of hydroxyapatite (e.g., hydroxyapatite derived from bone may be substituted with other ions such as fluoride, chloride, magnesium sodium, potassium, etc.), or combinations or derivatives thereof.

In some embodiments, the matrix has a thickness of from 0.25 mm to 5 mm, or from about 0.4 mm to about 2 mm, or 0.4 mm to about 1 mm. Clearly, different bone defects (e.g., osteochondral defects) may require different matrix thicknesses.

In some embodiments, the matrix has a density of between about 1.6 g/cm$^3$, and about 0.05 g/cm$^3$. In some embodiments, the matrix has a density of between about 1.1 g/cm$^3$, and about 0.07 g/cm$^3$. For example, the density may be less than about 1 g/cm$^3$, less than about 0.7 g/cm$^3$, less than about 0.6 g/cm$^3$, less than about 0.5 g/cm$^3$, less than about 0.4 g/cm$^3$, less than about 0.3 g/cm$^3$, less than about 0.2 g/cm$^3$, or less than about 0.1 g/cm$^3$.

The shape of the matrix may be tailored to the site at which it is to be situated. For example, it may be in the shape of a morsel, a plug, a pin, a peg, a cylinder, a block, a wedge, a sheet, etc.

In some embodiments, the diameter or diagonal of the matrix can range from 1 mm to 50 mm. In some embodiments, the diameter or diagonal of the matrix can range from 1 mm to 30 mm, or 5 mm to 10 mm which is small enough to fit through an endoscopic cannula, but large enough to minimize the number of matrices needed to fill a large the bone defect (e.g., osteochondral defect).

In some embodiments, the matrix may be made by injection molding, compression molding, blow molding, thermoforming, die pressing, slip casting, electrochemical machining, laser cutting, water jet machining, electrophoretic deposition, powder injection molding, sand casting, shell mold casting, lost tissue scaffold casting, plaster-mold casting, ceramic-mold casting, investment casting, vacuum casting, permanent-mold casting, slush casting, pressure casting, die casting, centrifugal casting, squeeze casting, rolling, forging, swaging, extrusion, shearing, spinning, powder metallurgy compaction or combinations thereof.

In some embodiments, a therapeutic agent (including one or more TRPV1 compound (e.g., capsaicinoid compound)) may be disposed on or in the matrix by hand by soaking, electrospraying, ionization spraying or impregnating, vibratory dispersion (including sonication), nozzle spraying, compressed-air-assisted spraying, brushing and/or pouring.

In some embodiments, the matrix may comprise sterile and/or preservative free material. The matrix can be implanted by hand or machine in procedures such as for example, laparoscopic, arthroscopic, neuroendoscopic, endoscopic, rectoscopic procedures or the like.

In some embodiments, the matrix can be in the form of a collagen sponge that can be spray coated or embedded with the TRPV1 compound (e.g., capsaicinoid compound), and as the sponge degrades, the TRPV1 compound (e.g., capsaicinoid compound) is released.

As shown in FIG. 1, the medical device, in this embodiment, may be in matrix form 101 comprising an implant body 100 including a surface that may provide an initial burst release of the TRPV1 compound (e.g., capsaicinoid compound). Therefore, on implantation, the matrix will immediately release the TRPV1 compound (e.g., capsaicinoid compound) to provide its therapeutic effect locally at the target tissue site. This is particularly beneficial to reduce or treat in postoperative pain.

In some embodiments, the initial burst surfaces can be disposed on the edges of the matrix so that upon contact with the target tissue site, the edges will begin to release the TRPV1 compound (e.g., capsaicinoid compound). In some embodiments, the core of the matrix can comprise dense, entangled polymers and have the TRPV1 compound (e.g., capsaicinoid compound) to provide slower release of the TRPV1 compound (e.g., capsaicinoid compound).

Alternatively, the TRPV1 compound (e.g., capsaicinoid compound) can be disposed homogenously throughout the matrix to provide continuous extended release of the TRPV1 compound (e.g., capsaicinoid compound). In some embodiments, the TRPV1 compound (e.g., capsaicinoid compound) can be layered in the matrix with some portions having different concentrations to provide burst release and then slower release of the TRPV1 compound (e.g., capsaicinoid compound) in areas that have dense crosslinked polymers, such as for example, in the core of the matrix.

While FIG. 1 depicts a matrix 101 in a rectangular form, alternate shapes and configurations may be contemplated. In further exemplary embodiments, the matrix may be a narrow tube for delivery through a catheter. For example, the matrix may be delivered percutaneously using a catheter through which it is inserted. Thus, the matrix may have dimensions suitable for receipt in the catheter. Optionally, the matrix may be stiffened to facilitate insertion into the catheter. Such stiffening may be achieved through choice of material for the matrix, by treating the material of the matrix, or other. In some embodiments, the matrix may be coated with a material to facilitate sliding engagement with the catheter.

Figure 2:
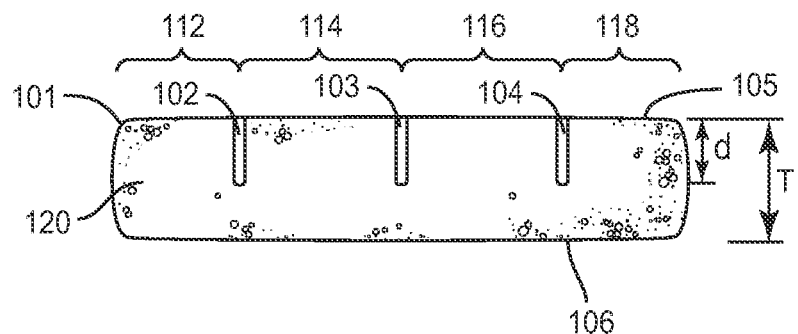
FIG. 2 provides a cross-sectional view of the implant body of FIG. 1 taken along line 2-2 and viewed in the direction of the arrows.
Figure 3:
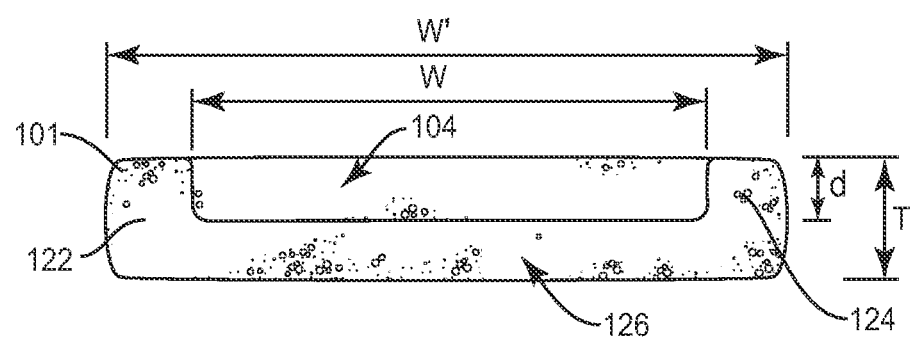
FIG. 3 provides a cross-sectional view of the implant body of FIG. 1 taken along line 3-3 and viewed in the direction of the arrows.

In the illustrative embodiment shown in FIGS. 1, 2 and 3, a medical device 100 having a matrix 101 is shown. This matrix can be, if desired, conformable to the target tissue site and broken into pieces to, for example, triangulate around a pain generator.

Matrix 101 comprises a biocompatible implant material 120 and includes separation-assist lines in the form of three score lines 102, 103, and 104, rendering the medical device 100 separable into implant body pieces 112, 114, 116, 118. Matrix 101 includes an upper surface 105, a lower surface 106, and side walls 107, 108, 109 and 110. These can be burst release surfaces that immediately release the TRPV1 compound (e.g., capsaicinoid compound). Alternatively, the TRPV1 compound (e.g., capsaicinoid compound) can be disposed in the core of the matrix that may contained entangled polymer to slow release of the TRPV1 compound (e.g., capsaicinoid compound).

In the illustrated device having implant body 100, a rectangular configuration is provided. This may include for example an equilateral rectangle (square) configuration wherein walls 107-110 each have the same dimension, or a non-equilateral rectangle wherein walls 107 and 108 are of a lesser dimension than walls 109 and 110. Thus, overall matrix 100 includes a length L, defined as the dimension of walls 109 and 110 in a first direction, a width W defined by the dimension of walls 107 and 108 in a first direction, and a thickness T defined by the dimension of walls 107-110 in a second direction generally perpendicular to the first directions noted above.

In certain embodiments, the length L of the overall implant body 100 will range from about 1 cm to about 15 cm, the width W will range from about 1 cm to about 20 cm, and the thickness T will range from about 0.5 cm to about 9 cm. Length L may range from about 2.5 to about 8 cm, width W may range from about 2.5 to about 8 cm, and thickness T may range from about 1 to about 10 cm.

As to volume, advantageous implant bodies 100 can have a total volume of at least about 2 cubic centimeters (cc), e.g. in the range of about 2 cc to about 100 cc, and more typically in the range of about 10 cc to about 50 cc, although both smaller and larger overall volumes may also be used. Similarly, the volume of the pieces into which the implant bodies are configured to be separated may range from about 1 cc to about 50 cc, more typically in the range of about 5 cc to about 20 cc, although other piece volumes will also be suitable in broader aspects of the present principles.

In some embodiments, implant bodies 100 have a modulus of elasticity in the range of about $1 \times 10'$ to about $6 \times 10^5$ dynes/$cm^2$, or $2 \times 10^4$ to about $5 \times 10^5$ dynes/$cm^2$, or $5 \times 10^4$ dynes/$cm^2$ to about $5 \times 10^5$ dynes/$cm^2$.

In some embodiments, the semi-solid or solid implant bodies 100 may comprise a polymer having a molecular weight, as shown by the inherent viscosity, from about 0.10 dL/g to about 1.2 dL/g or from about 0.10 dL/g to about 0.40 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.55 dL/g, about 0.50 to about 0.70 dL/g, about 0.55 to about 0.6 dL/g, about 0.60 to about 0.80 dL/g, about 0.70 to about 0.90 dL/g, about 0.80 to about 1.00 dL/g, about 0.90 to about 1.10 dL/g, about 1.0 to about 1.2 dL/g, about 1.1 to about 1.3 dL/g, about 1.2 to about 1.4 dL/g, about 1.3 to about 1.5 dL/g, about 1.4 to about 1.6 dL/g, about 1.5 to about 1.7 dL/g, about 1.6 to about 1.8 dL/g, about 1.7 to about 1.9 dL/g, or about 1.8 to about 2.1 dL/g.

In some embodiments, the drug depot shown as a matrix may have a burst release surface that releases about 10%, 15%, 20%, 25%, 30%, 35%, 45%, to about 50% of the TRPV1 compound (e.g., capsaicinoid compound) over 24 or 48 hours.

With reference now particularly to FIGS. 2 and 3, provided in FIG. 2 is a cross-sectional view taken along line 2-2 of FIG. 1 and viewed in the direction of the arrows, and provided in FIG. 3 is a cross-sectional view taken along line 3-3 of FIG. 1 and viewed in the direction of the arrows. As shown, score lines 102, 103 and 104 extend from upper surface 105 of implant body 100 partially through the thickness T of the implant body 100. These score lines in the illustrated embodiment thus extend a depth d, which is thus less than the thickness T of the implant body 100. Depth d can be any suitable portion or percentage of thickness T, but depth d will generally represent 20% to 90% of thickness T, and depth d may represent about 30% to about 80% of thickness T. In certain forms, depth d may range from about 40% to about 60% of thickness T. In one embodiment, the implant bodies may be layered with varying thicknesses at every layer. In further embodiments, the implant bodies may be layered having a uniform thickness at every layer.

The score lines 102, 103 and 104 also extend only partially across the width W of the implant body 100. In this manner, peripheral portions 122 and 124 will be provided at or near the periphery of implant body 100 and can serve to reinforce the overall integrity of implant body 100, for example relative to that integrity which would exist should score lines 102, 103 and 104 extend completely across the width W of implant body 100. Thus, peripheral portions 122 and 124 are relatively thicker than portion 126 in the region in which the score line 104 extends. It will be understood that similar structures and features will exist for other score lines such as 102 and 103. The score lines can, in some embodiments, allow the matrix to be folded back upon itself and then implanted.

Gel

In various embodiments, the TRPV1 compound (e.g., capsaicinoid compound) is administered in a gel. The gel may have a pre-dosed viscosity in the range of about 1 to about 2000 centipoise (cps), 1 to about 200 cps, or 1 to about 100 cps. After the gel is administered to the target site, the viscosity of the gel will increase and the gel will have a modulus of elasticity (Young's modulus) in the range of about $1 \times -10^2$ to about $6\times10^5$ dynes/cm$^2$, or $2\times10^4$ to about $5\times10^5$ dynes/cm$^2$, or $5\times10^4$ to about $5\times10^5$ dynes/cm$^2$.

In one embodiment, a depot comprises an adherent gel comprising capsaicinoid that is evenly distributed throughout the gel. The gel may be of any suitable type, as previously indicated, and should be sufficiently viscous so as to prevent the gel from migrating from the targeted delivery site once deployed; the gel should, in effect, "stick" or adhere to the targeted tissue site. The gel may, for example, solidify upon contact with the targeted tissue or after deployment from a targeted delivery system. The targeted delivery system may be, for example, a syringe, a catheter, needle or cannula or any other suitable device. The targeted delivery system may inject the gel into or on the targeted tissue site. The therapeutic agent may be mixed into the gel prior to the gel being deployed at the targeted tissue site. In various embodiments, the gel may be part of a two-component delivery system and when the two components are mixed, a chemical process is activated to form the gel and cause it to stick or to adhere to the target tissue.

In various embodiments, a gel is provided that hardens or stiffens after delivery. Typically, hardening gel formulations may have a pre-dosed modulus of elasticity in the range of about $1\times-10^2$ to about $3\times10^5$ dynes/cm$^2$, or $2\times10^4$ to about $2\times10^5$ dynes/cm$^2$, or $5\times10^4$ to about $1\times10^5$ dynes/cm$^2$. The post-dosed hardening gels (after delivery) may have a rubbery consistency and have a modulus of elasticity in the range of about $1\times-10^2$ to about $2\times10^6$ dynes/cm$^2$, or $1\times10^5$ to about $7\times10^5$ dynes/cm$^2$, or $2\times10^5$ to about $5\times10^5$ dynes/cm$^2$.

In various embodiments, for those gel formulations that contain a polymer, the polymer concentration may affect the rate at which the gel hardens (e.g., a gel with a higher concentration of polymer may coagulate more quickly than gels having a lower concentration of polymer). In various embodiments, when the gel hardens, the resulting matrix is solid but is also able to conform to the irregular surface of the tissue (e.g., recesses and/or projections in bone).

The percentage of polymer present in the gel may also affect the viscosity of the polymeric composition. For example, a composition having a higher percentage by weight of polymer is typically thicker and more viscous than a composition having a lower percentage by weight of polymer. A more viscous composition tends to flow more slowly. Therefore, a composition having a lower viscosity may be preferred in some instances. In some embodiments, the polymer comprises 20 wt. % to 90 wt. % of the formulation.

In various embodiments, the molecular weight of the gel can be varied by many methods known in the art. The choice of method to vary molecular weight is typically determined by the composition of the gel (e.g., polymer, versus non-polymer). For example in various embodiments, when the gel comprises one or more polymers, the degree of polymerization can be controlled by varying the amount of polymer initiators (e.g. benzoyl peroxide), organic solvents or activator (e.g. DMPT), crosslinking agents, polymerization agent, incorporation of chain transfer or chain capping agents and/or reaction time.

Suitable gel polymers may be soluble in an organic solvent. The solubility of a polymer in a solvent varies depending on the crystallinity, hydrophobicity, hydrogen-bonding and molecular weight of the polymer. Lower molecular weight polymers will normally dissolve more readily in an organic solvent than high-molecular weight polymers. A polymeric gel that includes a high molecular weight polymer tends to coagulate or solidify more quickly than a polymeric composition that includes a low-molecular weight polymer. Polymeric gel formulations that include high molecular weight polymers, also tend to have a higher solution viscosity than a polymeric gel that includes low-molecular weight polymers. In various embodiments, the molecular weight of the polymer can be a wide range of values. The average molecular weight of the polymer can be from about 1000 to about 10,000,000 Da; or about 1,000 to about 1,000,000 Da; or about 5,000 Da to about 500,000 Da; or about 10,000 Da to about 100,000 Da; or about 20,000 Da to 50,000 Da.

When the gel is designed to be a flowable gel, it can vary from low viscosity, similar to that of water, to high viscosity, similar to that of a paste, depending on the molecular weight and concentration of the polymer used in the gel. The viscosity of the gel can be varied such that the polymeric composition can be applied to a patient's tissues by any convenient technique, for example, by brushing, dripping, injecting, or painting. Different viscosities of the gel will depend on the technique used to apply the composition.

In various embodiments, the gel has an inherent viscosity (abbreviated as "I.V." and units are in deciliters/gram), which is a measure of the gel's molecular weight and degradation time (e.g., a gel with a high inherent viscosity has a higher molecular weight and may have a longer degradation time). Typically, when the polymers have similar components but different MWs, a gel with a high molecular weight provides a stronger matrix and the matrix takes more time to degrade. In contrast, a gel with a low molecular weight degrades more quickly and provides a softer matrix. In various embodiments, the gel has a molecular weight, as shown by the inherent viscosity, from about 0.10 dL/g to about 1.2 dL/g or from about 0.10 dL/g to about 0.40 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.50 dL/g, about 0.50 to about 0.70 dL/g, about 0.60 to about 0.80 dL/g, about 0.70 to about 0.90 dL/g, about 0.80 to about 1.00 dL/g, about 0.90 to about 1.10 dL/g, about 1.0 to about 1.2 dL/g, about 1.1 to about 1.3 dL/g, about 1.2 to about 1.4 dL/g, about 1.3 to about 1.5 dL/g, about 1.4 to about 1.6 dL/g, about 1.5 to about 1.7 dL/g, about 1.6 to about 1.8 dL/g, about 1.7 to about 1.9 dL/g, and about 1.8 to about 2.1 dL/g.

In some embodiments, when the polymer materials have different chemistries (e.g., high MW DLG 5050 and low MW DL), the high MW polymer may degrade faster than the low MW polymer.

In various embodiments, the gel can have a viscosity of about 300 to about 5,000 centipoise (cp). In other embodiments, the gel can have a viscosity of from about 5 to about 300 cps, from about 10 cps to about 50 cps, or from about 15 cps to about 75 cps at room temperature. The gel may optionally have a viscosity enhancing agent such as, for example, hydroxypropyl cellulose, hydroxypropyl methylcellulose, hydroxyethyl methylcellulose, carboxymethylcellulose and salts thereof, Carbopol, poly-(hydroxyethylmethacrylate), poly-(methoxyethylmethacrylate), poly(methoxyethoxyethyl methacrylate), polymethylmethacrylate (PMMA), methylmethacrylate (MMA), gelatin, polyvinyl alcohols, propylene glycol, mPEG, PEG 200, PEG 300, PEG 400, PEG 500, PEG 600, PEG 700, PEG 800, PEG 900, PEG 1000, PEG 1450, PEG 3350, PEG 4500, PEG 8000 or combinations thereof.

In various embodiments, the gel is a hydrogel made of high molecular weight biocompatible elastomeric polymers of synthetic or natural origin. A desirable property for the hydrogel to have is the ability to respond rapidly to mechanical stresses, particularly shears and loads, in the human body.

Hydrogels obtained from natural sources are particularly appealing because they are more likely to be biocompatible for in vivo applications. Suitable hydrogels include natural hydrogels, such as for example, gelatin, collagen, silk, elastin, fibrin and polysaccharide-derived polymers like agarose, and chitosan, glucomannan gel, hyaluronic acid, polysaccharides, such as cross-linked carboxyl-containing polysaccharides, or a combination thereof. Synthetic hydrogels include, but are not limited to those formed from polyvinyl alcohol, acrylamides such as polyacrylic acid and poly (acrylonitrile-acrylic acid), polyurethanes, polyethylene glycol (e.g., PEG 3350, PEG 4500, PEG 8000), silicone, polyolefins such as polyisobutylene and polyisoprene, copolymers of silicone and polyurethane, neoprene, nitrile, vulcanized rubber, poly (N-vinyl-2-pyrrolidone), acrylates such as poly(2-hydroxy ethyl methacrylate) and copolymers of acrylates with N-vinyl pyrolidone, N-vinyl lactams, polyacrylonitrile or combinations thereof. The hydrogel materials may further be cross-linked to provide further strength as needed. Examples of different types of polyurethanes include thermoplastic or thermoset polyurethanes, aliphatic or aromatic polyurethanes, polyetherurethane, polycarbonate-urethane or silicone polyetherurethane, or a combination thereof.

In various embodiments, rather than directly admixing the therapeutic agent into the gel, microspheres may be dispersed within the gel, the microspheres being loaded with the TRPV1 compound (e.g., capsaicinoid compound). In one embodiment, the microspheres provide for a sustained release of the TRPV1 compound (e.g., capsaicinoid compound). In yet another embodiment, the gel, which is biodegradable, prevents the microspheres from releasing the TRPV1 compound (e.g., capsaicinoid compound); the microspheres thus do not release the TRPV1 compound (e.g., capsaicinoid compound) until they have been released from the gel. For example, a gel may be deployed around a target tissue site (e.g., a nerve root). Dispersed within the gel may be a plurality of microspheres that encapsulate the desired therapeutic agent. Certain of these microspheres degrade once released from the gel, thus releasing the TRPV1 compound (e.g., capsaicinoid compound).

Microspheres, much like a fluid, may disperse relatively quickly, depending upon the surrounding tissue type, and hence disperse the TRPV1 compound (e.g., capsaicinoid compound). In some situations, this may be desirable; in others, it may be more desirable to keep the TRPV1 compound (e.g., capsaicinoid compound) tightly constrained to a well-defined target site. The present invention also contemplates the use of adherent gels to so constrain dispersal of the therapeutic agent. These gels may be deployed, for example, in a disc space, in a spinal canal, or in surrounding tissue.

Drug Delivery

It will be appreciated by those with skill in the art that the depot can be administered to the target site using a "cannula" or "needle" that can be a part of a drug delivery device e.g., a syringe, a gun drug delivery device, or any medical device suitable for the application of a drug to a targeted organ or anatomic region. The cannula or needle of the drug depot device is designed to cause minimal physical and psychological trauma to the patient.

Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The dimensions of the hollow cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas. In various embodiments, the cannula or needle may be inserted using a transforaminal approach in the spinal foramen space, for example, along an inflamed nerve root and the drug depot implanted at this site for treating the condition. Typically, the transforaminal approach involves approaching the intervertebral space through the intervertebral foramina.

Some examples of lengths of the cannula or needle may include, but are not limited to, from about 15 to 150 mm in length, for example, about 65 mm for epidural pediatric use, about 85 mm for a standard adult and about 110 mm for an obese adult patient. The thickness of the cannula or needle will also depend on the site of implantation. In various embodiments, the thickness includes, but is not limited to, from about 0.05 to about 1.655 (mm). The gauge of the cannula or needle may be the widest or smallest diameter or a diameter in between for insertion into a human or animal body. The widest diameter is typically about 14 gauge, while the smallest diameter is about 22 gauge. In various embodiments the gauge of the needle or cannula is about 18 to about 22 gauge.

In various embodiments, like the drug depot and/or gel, the cannula or needle includes dose radiographic markers that indicate location at or near the site beneath the skin, so that the user may accurately position the depot at or near the site using any of the numerous diagnostic imaging procedures. Such diagnostic imaging procedures include, for example, X-ray imaging or fluoroscopy. Examples of such radiographic markers include, but are not limited to, barium, bismuth, tantalum, tungsten, iodine, calcium, and/or metal beads or particles.

In various embodiments, the needle or cannula may include a transparent or translucent portion that can be visualizable by ultrasound, fluoroscopy, X-ray, or other imaging techniques. In such embodiments, the transparent or translucent portion may include a radiopaque material or ultrasound responsive topography that increases the contrast of the needle or cannula relative to the absence of the material or topography.

The drug depot/matrix, and/or medical device to administer the drug may be sterilizable. In various embodiments, one or more components of the drug depot, and/or medical device to administer the drug are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the drug depot is included in a gel.

Other methods may also be used to sterilize the depot and/or one or more components of the device, including, but not limited to, gas sterilization, such as, for example, with ethylene oxide or steam sterilization.

In various embodiments, a kit is provided that may include additional parts along with the drug depot and/or medical device combined together to be used to implant the drug depot. The kit may include the drug depot device in a first compartment. The second compartment may include a canister holding the drug depot and any other instruments needed for the localized drug delivery. A third compartment may include gloves, drapes, wound dressings and other procedural supplies for maintaining sterility of the implanting process, as well as an instruction booklet. A fourth compartment may include additional cannulas and/or needles. A fifth compartment may include an agent for radiographic imaging. Each tool may be separately packaged in a plastic pouch that is radiation sterilized. A cover of the kit may include illustrations of the implanting procedure and a clear plastic cover may be placed over the compartments to maintain sterility. In some embodiments, a kit is provided with instruction to use an injectable drug from another kit.

In various embodiments, a method for delivering a therapeutic agent into a site of a patient is provided, the method comprising inserting a cannula at or near a target tissue site and implanting the drug depot at the target site beneath the skin of the patient and brushing, dripping, injecting, or painting the gel in the target site to hold or have the drug depot adhere to the target site. In this way unwanted migration of the drug depot away from the target site is reduced or eliminated.

In various embodiments, to administer the gel having the drug depot dispersed therein to the desired site, first the cannula or needle can be inserted through the skin and soft tissue down to the target tissue site and the gel administered at or near the target site. In those embodiments where the drug depot is separate from the gel, first the cannula or needle can be inserted through the skin and soft tissue down to the site of injection and one or more base layer(s) of gel can be administered to the target site. Following administration of the one or more base layer(s), the drug depot can be implanted on or in the base layer(s) so that the gel can hold the depot in place or reduce migration. If required, a subsequent layer or layers of gel can be applied on the drug depot to surround the depot and further hold it in place. Alternatively, the drug depot may be implanted first and then the gel placed around the drug depot to hold it in place. By using the gel, accurate and precise implantation of a drug depot can be accomplished with minimal physical and psychological trauma to the patient. The gel also avoids the need to suture the drug depot to the target site reducing physical and psychological trauma to the patient.

In various embodiments, when the target site comprises a spinal region, a portion of fluid (e.g., spinal fluid, etc.) can be withdrawn from the target site through the cannula or needle first and then the depot administered (e.g., placed, dripped, injected, or implanted, etc.). The target site will re-hydrate (e.g., replenishment of fluid) and this aqueous environment will cause the drug to be released from the depot.

In one exemplary embodiment the depot is suitable for use in treating spasticity (e.g., neuropathic pain management) and/or to treat conditions (e.g., sciatica). The drug depot may be inserted using a cannula or needle beneath the skin of a patient to a spinal site (e.g., spinal disc space, spinal canal, soft tissue surrounding the spine, nerve root, etc.) and one or more drug depots are delivered to various sites along the spine. In this way, when several drug depots are to be implanted, they are implanted in a manner that optimizes location, accurate spacing, and drug distribution.

Although the spinal site is shown, as described above, the drug depot can be delivered to any site beneath the skin, including, but not limited to, at least one muscle, ligament, tendon, cartilage, spinal disc, spinal foraminal space, near the spinal nerve root, or spinal canal.

In some embodiments, it is preferable to co-administer the TRPV1 compound (e.g., capsaicinoid compound) with an antagonist to counteract undesirable effects, for example the blood pressure decrease that can be caused by TRPV1 compound (e.g., capsaicinoid compound). Exemplary antagonists include but are not limited to phentolamine, yohimbine, tolazoline and piperoxane. Additionally, compounds such as 5-fluorodeoxyuridine (FUDR) and 3,4 dehydroprolene may also be included. These compounds may prevent or reduce glial and fibroblastic scar formation associated with some types of surgeries.

The TRPV1 compound (e.g., capsaicinoid compound) formulation of the present application may be used as medicaments in the form of pharmaceutical preparations. The preparations may be formed in an administration with a suitable pharmaceutical carrier that may be solid or liquid and organic or inorganic, and placed in the appropriate form for parenteral or other administration as desired. As persons of ordinary skill are aware, known carriers include but are not limited to water, saline solution, gelatin, lactose, starches, stearic acid, magnesium stearate, sicaryl alcohol, talc, vegetable oils, benzyl alcohols, gums, waxes, propylene glycol, polyalkylene glycols and other known carriers for medicaments.

Parenteral administration may additionally include, for example, an infusion pump that administers a pharmaceutical composition (e.g., analgesic and anti-inflammatory combination) through a catheter near the spine or one or more inflamed joints, an implantable mini-pump that can be inserted at or near the target site, an implantable controlled release device or sustained release delivery system that can release a certain amount of the statin per hour or in intermittent bolus doses. One example of a suitable pump for use is the SynchroMed® (Medtronic, Minneapolis, Minn.) pump. This pump has three sealed chambers. One contains an electronic module and battery. The second contains a peristaltic pump and drug reservoir. The third contains an inert gas that provides the pressure needed to force the pharmaceutical composition into the peristaltic pump. To fill the pump, the pharmaceutical composition is injected through the reservoir fill port to the expandable reservoir. The inert gas creates pressure on the reservoir, and the pressure forces the pharmaceutical composition through a filter and into the pump chamber. The pharmaceutical composition is then pumped out of the device from the pump chamber and into the catheter, which will direct it for deposit at the target site. The rate of delivery of pharmaceutical composition is controlled by a microprocessor. This allows the pump to be used to deliver similar or different amounts of pharmaceutical composition continuously, continually, at specific times, or at set intervals between deliveries.

Another embodiment is directed to a method for treating a mammal suffering from pain, said method comprising administering a therapeutically effective amount of a TRPV1 compound (e.g., capsaicinoid compound) at a target site beneath the skin. The TRPV1 compound (e.g., capsaicinoid compound) may for example be administered locally to the target tissue site as a drug depot.

In some embodiments, the TRPV1 compound (e.g., capsaicinoid compound) is encapsulated in a plurality of depots comprising microparticles, microspheres, microcapsules, and/or microfibers.

In some embodiments there is a method for making an implantable drug depot. The method may comprise combining a biocompatible polymer and a therapeutically effective amount of TRPV1 compound (e.g., capsaicinoid compound) and forming the implantable drug depot from the combination.

In some embodiments, the TRPV1 compound (e.g., capsaicinoid compound) is suitable for parenteral administration. The term "parenteral" as used herein refers to modes of administration that bypass the gastrointestinal tract, and include for example, intravenous, intramuscular, continuous or intermittent infusion, intraperitoneal, intrasternal, subcutaneous, intra-operatively, intrathecally, intradiscally, peridiscally, epidurally, perispinally, intraarticular injection or combinations thereof. In some embodiments, the injection is intrathecal, which refers to an injection into the spinal canal (intrathecal space surrounding the spinal cord). An injection may also be into a muscle or other tissue.

In various embodiments, the drug depot comprising the TRPV1 compound (e.g., capsaicinoid compound), can be made by combining a biocompatible polymer and a therapeutically effective amount of the TRPV1 compound (e.g., capsaicinoid compound) and forming the implantable drug depot from the combination.

Various techniques are available for forming at least a portion of a drug depot from the biocompatible polymer(s), therapeutic agent(s), and optional materials, including solution processing techniques and/or thermoplastic processing techniques. Where solution processing techniques are used, a solvent system is typically selected that contains one or more solvent species. The solvent system is generally a good solvent for at least one component of interest, for example, biocompatible polymer and/or therapeutic agent. The particular solvent species that make up the solvent system can also be selected based on other characteristics, including drying rate and surface tension.

Solution processing techniques include solvent casting techniques, spin coating techniques, web coating techniques, solvent spraying techniques, dipping techniques, techniques involving coating via mechanical suspension, including air suspension (e.g., fluidized coating), ink jet techniques and electrostatic techniques. Where appropriate, techniques such as those listed above can be repeated or combined to build up the depot to obtain the desired release rate and desired thickness.

In various embodiments, a solution containing solvent and biocompatible polymer are combined and placed in a mold of the desired size and shape. In this way, polymeric regions, including barrier layers, lubricious layers, and so forth can be formed. If desired, the solution can further comprise, one or more of the following: a TRPV1 compound (e.g., capsaicinoid compound) and other therapeutic agent(s) and other optional additives such as radiographic agent(s), etc. in dissolved or dispersed form. This results in a polymeric matrix region containing these species after solvent removal. In other embodiments, a solution containing solvent with dissolved or dispersed therapeutic agent is applied to a pre-existing polymeric region, which can be formed using a variety of techniques including solution processing and thermoplastic processing techniques, whereupon the therapeutic agent is imbibed into the polymeric region.

Thermoplastic processing techniques for forming the depot or portions thereof include molding techniques (for example, injection molding, rotational molding, and so forth), extrusion techniques (for example, extrusion, co-extrusion, multi-layer extrusion, and so forth) and casting.

Thermoplastic processing in accordance with various embodiments comprises mixing or compounding, in one or more stages, the biocompatible polymer(s) and one or more of the following: a TRPV1 compound (e.g., capsaicinoid compound), optional additional therapeutic agent(s), radiographic agent(s), and so forth. The resulting mixture is then shaped into an implantable drug depot. The mixing and shaping operations may be performed using any of the conventional devices known in the art for such purposes.

During thermoplastic processing, there exists the potential for the therapeutic agent(s) to degrade, for example, due to elevated temperatures and/or mechanical shear that are associated with such processing. For example, the TRPV1 compound (e.g., capsaicinoid compound) may undergo substantial degradation under ordinary thermoplastic processing conditions. Hence, processing is preferably performed under modified conditions, which prevent the substantial degradation of the therapeutic agent(s). Although it is understood that some degradation may be unavoidable during thermoplastic processing, degradation is generally limited to 10% or less. Among the processing conditions that may be controlled during processing to avoid substantial degradation of the therapeutic agent(s) are temperature, applied shear rate, applied shear stress, residence time of the mixture containing the therapeutic agent, and the technique by which the polymeric material and the therapeutic agent(s) are mixed.

Mixing or compounding biocompatible polymer with therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives (e.g., therapeutic agent(s), inactive ingredients, etc.) to form a mixture. A common way of doing so is to apply mechanical shear to a mixture of the biocompatible polymer(s) and additive(s). Devices in which the biocompatible polymer(s) and additive(s) may be mixed in this fashion include devices such as single screw extruders, twin screw extruders, banbury mixers, high-speed mixers, ross kettles, and so forth.

Any of the biocompatible polymer(s) and various additives may be premixed prior to a final thermoplastic mixing and shaping process, if desired (e.g., to prevent substantial degradation of the therapeutic agent among other reasons).

For example, in various embodiments, a biocompatible polymer is precompounded with a radiographic agent (e.g., radio-opacifying agent) under conditions of temperature and mechanical shear that would result in substantial degradation of the therapeutic agent, if it were present. This precompounded material is then mixed with therapeutic agent under conditions of lower temperature and mechanical shear, and the resulting mixture is shaped into the TRPV1 compound (e.g., capsaicinoid compound) containing drug depot. Conversely, in another embodiment, the biocompatible polymer can be precompounded with the therapeutic agent under conditions of reduced temperature and mechanical shear. This precompounded material is then mixed with, for example, a radio-opacifying agent, also under conditions of reduced temperature and mechanical shear, and the resulting mixture is shaped into the drug depot.

The conditions used to achieve a mixture of the biocompatible polymer and therapeutic agent and other additives will depend on a number of factors including, for example, the specific biocompatible polymer(s) and additive(s) used, as well as the type of mixing device used.

As an example, different biocompatible polymers will typically soften to facilitate mixing at different temperatures. For instance, where a depot is formed comprising PLGA or PLA polymer, a radio-opacifying agent (e.g., bismuth subcarbonate), and a therapeutic agent prone to degradation by heat and/or mechanical shear (e.g., capsaicinoid compound), in various embodiments, the PGLA or PLA can be premixed with the radio-opacifying agent at temperatures of about, for example, 150° C. to 170° C. The therapeutic agent is then combined with the premixed composition and subjected to further thermoplastic processing at conditions of temperature and mechanical shear that are substantially lower than is typical for PGLA or PLA compositions. For example, where extruders are used, barrel temperature, volumetric output are typically controlled to limit the shear and therefore to prevent substantial degradation of the therapeutic agent(s). For instance, the therapeutic agent and premixed composition can be mixed/compounded using a twin screw extruder at substantially lower temperatures (e.g., 100-105° C.), and using substantially reduced volumetric output (e.g., less than 30% of full capacity, which generally corresponds to a volumetric output of less than 200 cc/min). It is noted that this processing temperature is well below the melting points of the TRPV1 compound (e.g., capsaicinoid compound) because processing at or above these temperatures will result in substantial therapeutic agent degradation. It is further noted that in certain embodiments, the processing temperature will be below the melting point of all bioactive compounds within the composition, including the therapeutic agent. After compounding, the resulting depot is shaped into the desired form, also under conditions of reduced temperature and shear.

In other embodiments, biodegradable polymer(s) and one or more therapeutic agents are premixed using non-thermoplastic techniques. For example, the biocompatible polymer can be dissolved in a solvent system containing one or more solvent species. Any desired agents (for example, a radio-opacifying agent, a therapeutic agent, or both radio-opacifying agent and therapeutic agent) can also be dissolved or dispersed in the solvents system. Solvent is then removed from the resulting solution/dispersion, forming a solid material. The resulting solid material can then be granulated for further thermoplastic processing (for example, extrusion) if desired.

As another example, the therapeutic agent can be dissolved or dispersed in a solvent system, which is then applied to a pre-existing drug depot (the pre-existing drug depot can be formed using a variety of techniques including solution and thermoplastic processing techniques, and it can comprise a variety of additives including a radio-opacifying agent and/or viscosity enhancing agent), whereupon the therapeutic agent is imbibed on or in the drug depot. As above, the resulting solid material can then be granulated for further processing, if desired.

Typically, an extrusion process may be used to form the drug depot comprising a biocompatible polymer(s), therapeutic agent(s) and radio-opacifying agent(s). Co-extrusion may also be employed, which is a shaping process that can be used to produce a drug depot comprising the same or different layers or regions (for example, a structure comprising one or more polymeric matrix layers or regions that have permeability to fluids to allow immediate and/or sustained drug release). Multi-region depots can also be formed by other processing and shaping techniques such as co-injection or sequential injection molding technology.

In various embodiments, the depot that may emerge from the thermoplastic processing (e.g., pellet) is cooled. Examples of cooling processes include air cooling and/or immersion in a cooling bath. In some embodiments, a water bath is used to cool the extruded depot. However, where a water-soluble therapeutic agent such as a TRPV1 compound (e.g., capsaicinoid compound) is used, the immersion time should be held to a minimum to avoid unnecessary loss of therapeutic agent into the bath.

In various embodiments, immediate removal of water or moisture by use of ambient or warm air jets after exiting the bath will also prevent re-crystallization of the drug on the depot surface, thus controlling or minimizing a high drug dose "initial burst" or "bolus dose" upon implantation or insertion if this is release profile is not desired.

In various embodiments, the drug depot can be prepared by mixing or spraying the drug with the polymer and then molding the depot to the desired shape. In various embodiments, capsaicinoid is used and mixed or sprayed with the PLGA or PEG550 polymer, and the resulting depot may be formed by extrusion and dried.

In various embodiments, there is a pharmaceutical formulation comprising: a TRPV1 compound (e.g., capsaicinoid compound), wherein the TRPV1 compound (e.g., capsaicinoid compound) comprises from about 0.1 wt. % to about 30 wt. % of the formulation, and at least one biodegradable polymer. In some embodiments, the TRPV1 compound (e.g., capsaicinoid compound) comprises from about 3 wt. % to about 20 wt. %, about 3 wt. % to about 18 wt. %, about 5 wt. % to about 15 wt. % or about 7.5 wt. % to about 12.5 wt. % of the formulation. By way of example, when using a 5%-15% TRPV1 compound (e.g., capsaicinoid compound), the mole ratio of capsaicinoid to polymer would be from approximately 16-53 when using an approximately 80 kDalton polymer that has a 267 grams/mole ratio. By way of another example, when using a 5%-15% capsaicinoid base in the composition, the mole ratio of capsaicinoid base to polymer would be from approximately 18-61 with a mole mass of 230 g/mol.

In some embodiments, the capsaicinoid prodrug can be in the formulation with or without capsaicinoid. In some embodiments, the capsaicinoid prodrug is in the formulation at about 1%, 5%, 10%, 15%, 20%, 25%, 30%, 35%, or 40% by weight based on the total weight of the formulation.

In some embodiments, the drug depot comprises at least one biodegradable material in a wt % of about 99.5%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 76%, 75%, 74%, 73%, 72%, 71%, 70%, 65%, 60%, 55%, 50%, 45%, 35%, 25%, 20%, 15%, 10%, or 5% based on the total weight of the depot and the remainder is active and/or inactive pharmaceutical ingredients.

In some embodiments, the at least one biodegradable polymer comprises poly(lactic-co-glycolide) (PLGA) or poly(orthoester) (POE) or a combination thereof. The poly(lactic-co-glycolide) may comprise a mixture of polyglycolide (PGA) and polylactide and in some embodiments, in the mixture, there is more polylactide than polyglycolide. In various embodiments there is 100% polylactide and 0% polyglycolide; 95% polylactide and 5% polyglycolide; 90% polylactide and 10% polyglycolide; 85% polylactide and 15% polyglycolide; 80% polylactide and 20% polyglycolide; 75% polylactide and 25% polyglycolide; 70% polylactide and 30% polyglycolide; 65% polylactide and 35% polyglycolide; 60% polylactide and 40% polyglycolide; 55% polylactide and 45% polyglycolide; 50% polylactide and 50% polyglycolide; 45% polylactide and 55% polyglycolide; 40% polylactide and 60% polyglycolide; 35% polylactide and 65% polyglycolide; 30% polylactide and 70% polyglycolide; 25% polylactide and 75% polyglycolide; 20% polylactide and 80% polyglycolide; 15% polylactide and 85% polyglycolide; 10% polylactide and 90% polyglycolide; 5% polylactide and 95% polyglycolide; and 0% polylactide and 100% polyglycolide.

In various embodiments that comprise both polylactide and polyglycolide; there is at least 95% polylactide; at least 90% polylactide; at least 85% polylactide; at least 80% polylactide; at least 75% polylactide; at least 70% polylactide; at least 65% polylactide; at least 60% polylactide; at least 55%; at least 50% polylactide; at least 45% polylactide; at least 40% polylactide; at least 35% polylactide; at least 30% polylactide; at least 25% polylactide; at least 20% polylactide; at least 15% polylactide; at least 10% polylactide; or at least 5% polylactide; and the remainder of the biopolymer is polyglycolide.

In various embodiments, the drug particle size (e.g., TRPV1 compound (e.g., capsaicinoid compound)) is from about 5 to 30 micrometers, however, in various embodiments ranges from about 1 micron to 250 microns may be used. In some embodiments, the biodegradable polymer comprises at least 50 wt. %, at least 60 wt. %, at least 70 wt. %, at least 80 wt. % of the formulation, at least 85 wt. % of the formulation, at least 90 wt. % of the formulation, at least 95 wt. % of the formulation or at least 97 wt. % of the formulation. In some embodiments, the at least one biodegradable polymer and the TRPV1 compound (e.g., capsaicinoid compound) are the only components of the pharmaceutical formulation.

In some embodiments, at least 75% of the particles have a size from about 10 micrometer to about 200 micrometers. In some embodiments, at least 85% of the particles have a size from about 10 micrometer to about 200 micrometers. In some embodiments, at least 95% of the particles have a size from about 10 micrometer to about 200 micrometers. In some embodiments, all of the particles have a size from about 10 micrometer to about 200 micrometers.

In some embodiments, at least 75% of the particles have a size from about 20 micrometer to about 180 micrometers. In some embodiments, at least 85% of the particles have a size from about 20 micrometers to about 180 micrometers. In some embodiments, at least 95% of the particles have a size from about 20 micrometer to about 180 micrometers. In some embodiments, all of the particles have a size from about 20 micrometer to about 180 micrometers. In some embodiments, at least 80% of the particles have a size from 5 microns to about 100 microns on a volume basis.

In some embodiments, there is a pharmaceutical formulation comprising: a TRPV1 compound (e.g., capsaicinoid compound) comprising from about 0.1 wt. % to about 30 wt. % of the formulation, and at least one biodegradable polymer, wherein the at least one biodegradable polymer comprises poly(lactide-co-glycolide) (or poly(lactic-co-glycolic acid)) or poly(orthoester) or a combination thereof, and said at least one biodegradable polymer comprises at least 70 wt. % of said formulation.

In some embodiments, there is a pharmaceutical formulation comprising a TRPV1 compound (e.g., capsaicinoid compound), wherein the TRPV1 compound (e.g., capsaicinoid compound) comprises from about 0.1 wt. % to about 30 wt. % of the formulation and a polymer comprises at least 70% of the formulation. In some embodiments, the polymer in this formulation is polyorthoester.

In some embodiments, the formulation comprises a drug depot that comprises a biodegradable polyorthoester. The mechanism of the degradation process of the polyorthoester can be hydrolytical or enzymatical in nature, or both. In various embodiments, the degradation can occur either at the surface of the drug depot (heterogeneous or surface erosion) or uniformly throughout the drug delivery system depot (homogeneous or bulk erosion). Polyorthoester can be obtained from A.P. Pharma, Inc. (Redwood City, Calif.) or through the reaction of a bis(ketene acetal) such as 3,9-diethylidene-2,4,8,10-tetraoxospiro[5,5]undecane (DETOSU) with suitable combinations of diol(s) and/or polyol(s) such as 1,4-trans-cyclohexanedimethanol and 1,6-hexanediol or by any other chemical reaction that produces a polymer comprising orthoester moieties.

In some embodiments, there are methods for treating acute pain. These methods comprise: administering a pharmaceutical composition to an organism, wherein said pharmaceutical composition (e.g., TRPV1 compound (e.g., capsaicinoid compound)) comprises from about 0.1 wt. % to about 30 wt. % of the formulation, and at least one biodegradable polymer. In some embodiments, the loading is from about 1 wt % to about 25 wt %, or about 5 wt. % to about 10 wt. %. In some embodiments, the loading is from about 10 wt. % to about 20 wt. %.

In some embodiment there is a higher loading of the TRPV1 compound (e.g., capsaicinoid compound), e.g., at least 20 wt. %, at least 30 wt. %, at least 40 wt. %, at least 50 wt. %, at least 60 wt. %, at least 70 wt. %, at least 80 wt. %, or at least 90 wt. %.

A strategy of triangulation may be effective when administering these pharmaceutical formulations. Thus, a plurality (at least two, at least three, at least four, at least five, at least six, at least seven, etc.) drug depots comprising the pharmaceutical formulations may be placed around the target tissue site (also known as the pain generator or pain generation site) such that the target tissue site falls within a region that is either between the formulations when there are two, or within an area whose perimeter is defined by a set of plurality of formulations.

In some embodiments, the formulations are slightly rigid with varying length, widths, diameters, etc. For example, certain formulations may have a diameter of 0.50 mm and a length of 4 mm. It should be noted that particle size may be altered by techniques such as mort and pestle, jet-drying or jet milling.

The dosage may be from approximately 0.0005 to approximately 960 µg/day. Additional dosages of the TRPV1 compound (e.g., capsaicinoid compound) include from approximately 0.0005 to approximately 900 µg/day; approximately 0.0005 to approximately 500 µg/day; approximately 0.0005 to approximately 250 µg/day; approximately 0.0005 to approximately 100 µg/day; approximately 0.0005 to approximately 75 µg/day; approximately 0.001 to approximately 70 µg/day; approximately 0.001 to approximately 65 µg/day;

approximately 0.001 to approximately 60 µg/day; approximately 0.001 to approximately 55 µg/day; approximately 0.001 to approximately 50 µg/day; approximately 0.001 to approximately 45 µg/day; approximately 0.001 to approximately 40 µg/day; approximately 0.001 to approximately 35 µg/day; approximately 0.0025 to approximately 30 µg/day; approximately 0.0025 to approximately 25 µg/day; approximately 0.0025 to approximately 20 µg/day; approximately 0.0025 to approximately 15 µg/day; approximately 0.0025 to approximately 10 µg/day; approximately 0.0025 to approximately 5 µg/day; and approximately 0.0025 to approximately 2.5 µg/day. In another embodiment, the dosage of the TRPV1 compound (e.g., capsaicinoid compound) is from approximately 0.005 to approximately 15 µg/day. In another embodiment, the dosage of the TRPV1 compound (e.g., capsaicinoid compound) is from approximately 0.005 to approximately 10 µg/day. In another embodiment, the dosage of the TRPV1 compound (e.g., capsaicinoid compound) is from approximately 0.005 to approximately 5 µg/day. In another embodiment, the dosage of the TRPV1 compound (e.g., capsaicinoid compound) is from approximately 0.005 to 2.5 µg/day. In some embodiments, the amount of the TRPV1 compound (e.g., capsaicinoid compound) is between 40 and 600 µg/day. In some embodiments, the amount of the TRPV1 compound (e.g., capsaicinoid compound) is between 200 and 400 µg/day.

In some embodiments, the therapeutically effective dosage amount (e.g., TRPV1 compound (e.g., capsaicinoid compound) dose) and the release rate profile are sufficient to reduce inflammation and/or pain for a period of at least one day, for example, 1-90 days, 1-10 days, 1-3 days, 3-7 days, 3-12 days; 3-14 days, 7-10 days, 7-14 days, 7-21 days, 7-30 days, 7-50 days, 7-90 days, 7-140 days, 14-140 days, 3 days to 135 days, 3 days to 180 days, or 3 days to 6 months or 1 year or longer.

In some embodiments the TRPV1 compound (e.g., capsaicinoid compound) in the depot is designed for a bolus dose or burst dose within 1, 2, or 3 days after implantation to provide an immediate release of the TRPV1 compound (e.g., capsaicinoid compound) for treatment of pain and/or inflammation.

In some embodiments, the TRPV1 compound (e.g., capsaicinoid compound) depot is administered parenterally, e.g., by injection. In some embodiments, the injection is intrathecal, which refers to an injection into the spinal canal (intrathecal space surrounding the spinal cord). An injection may also be into a muscle or other tissue. In other embodiments, the TRPV1 compound (e.g., capsaicinoid compound) depot is administered by placement into an open patient cavity during surgery.

In some embodiments, the drug depot (i) comprises one or more immediate release layer(s) that is capable of releasing about 5% to about 20% of the TRPV1 compound (e.g., capsaicinoid compound) relative to a total amount of the TRPV1 compound (e.g., capsaicinoid compound) loaded in the drug depot over a first period of up to 48 hours and (ii) one or more sustain release layer(s) that is capable of releasing about 21% to about 99% of the TRPV1 compound (e.g., capsaicinoid compound) relative to a total amount of the TRPV1 compound (e.g., capsaicinoid compound) loaded in the drug depot over a subsequent period of up to 3 days to 90 days, 150 days, 180 days, or 6 months to 1 year.

In some embodiments, there is a drug depot comprising a TRPV1 compound (e.g., capsaicinoid compound) and a polymer, wherein the polymer is one more of various embodiments, the drug depot comprises poly(lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone or a combination thereof.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An implantable device for reducing or treating pain in a patient in need of such treatment, the implantable device comprising a transient receptor potential cation channel subfamily V member 1 (TRPV1) compound comprising a capsaicinoid compound in an amount of about 55 wt. % of the implantable device, and at least one biodegradable polymer, wherein the implantable device is capable of releasing the TRPV 1 compound over a period of at least three days, wherein the at least one biodegradable polymer comprises collagen in sponge matrix form that is soaked or sprayed with the compound, and the collagen sponge comprises a burst surface on edges of the collagen sponge that release about 35% of the TRPV1 compound over 24 hours, and the sponge matrix has a porosity of at least about 70%.

2. An implantable device according to claim 1, wherein the capsaicinoid compound comprises capsaicin, nordihydrocapsaicin, dihydrocapsaicin, homodihydrocapsaicin, homocapsaicin, nonivamide or a combination thereof.

3. An implantable device according to claim 1, wherein said capsaicinoid compound is in the form of capsaicin hydrochloride or a mixture of capsaicin base and a hydrochloride salt.

4. An implantable device according to claim 1, wherein the drug depot releases: a bolus dose of the capsaicinoid compound at a site beneath the skin.

5. An implantable drug depot for reducing or treating pain in a patient in need of such treatment, the implantable drug depot comprising a capsaicinoid compound in an amount of about 55 wt. % of the drug depot and at least one polymer, wherein the at least one polymer comprises collagen in sponge matrix form that is soaked or sprayed with the capsaicinoid compound, and the collagen sponge comprises a burst surface on edges of the collagen sponge that release about 35% of the TRPV1 compound over 24 hours, and the sponge matrix has a porosity of at least about 70%.

6. An implantable drug depot according to claim 5, wherein the drug depot is in the form of a sponge matrix that comprises a plurality of separation-assist lines defined in the sponge matrix, the separation-assist lines configured to facilitate separation of the sponge matrix into a plurality of pieces.

7. A method for treating acute pain, wherein the method comprises implanting a drug depot in an organism to reduce or treat pain, wherein said drug depot comprises the implantable device of claim 1.

8. A method according to claim 7, wherein the capsaicinoid compound comprises capsaicin, nordihydrocapsaicin, dihydrocapsaicin, homodihydrocapsaicin, homocapsaicin, nonivamide or a combination thereof.

9. A method according to claim 8, wherein said capsaicinoid compound is in the form of capsaicin hydrochloride or a mixture of capsaicin and a hydrochloride salt or an insoluble fatty acid salt.

10. A method according to claim 7, wherein said implanting comprises applying said depot at a plurality of sites that triangulate a pain generator.

11. An implantable device according to claim 1, wherein the implantable device comprises an excipient comprising mannitol.

\* \* \* \* \*

UNITED STATES PATENT AND TRADEMARK OFFICE
CERTIFICATE OF CORRECTION

PATENT NO. : 9,211,274 B2
APPLICATION NO. : 13/363469
DATED : December 15, 2015
INVENTOR(S) : Moore et al.

It is certified that error appears in the above-identified patent and that said Letters Patent is hereby corrected as shown below:

On the Title Page, in Item (57), under "ABSTRACT", in Column 2, Line 6, delete "spondilothesis," and insert -- spondylothesis, --, therefor.

Specification

In Column 2, Line 3, delete "spondilothesis," and insert -- spondylothesis, --, therefor.

In Column 8, Line 34, delete "norhydrocapsaicin," and insert -- nordihydrocapsaicin, --, therefor.

In Column 10, Line 27, delete "glycollic," and insert -- glycolic, --, therefor.

In Column 11, Line 18, delete "palmeate" and insert -- palmitate --, therefor.

In Column 12, Line 7, delete "bescylate," and insert -- besylate, --, therefor.

In Column 12, Line 27, delete "basilicimab)," and insert -- basiliximab), --, therefor.

Signed and Sealed this
Fourteenth Day of June, 2016

Michelle K. Lee
*Director of the United States Patent and Trademark Office*